(12) United States Patent
Ooe

(10) Patent No.: US 9,720,006 B2
(45) Date of Patent: Aug. 1, 2017

(54) AUTOMATIC ANALYZING APPARATUS

(75) Inventor: Naoki Ooe, Otawara (JP)

(73) Assignee: Toshiba Medical Systems Corporation, Otawara-shi (JP)

(*) Notice: Subject to any disclaimer, the term of this patent is extended or adjusted under 35 U.S.C. 154(b) by 494 days.

(21) Appl. No.: 12/552,522

(22) Filed: Sep. 2, 2009

(65) Prior Publication Data

US 2010/0054997 A1  Mar. 4, 2010

(30) Foreign Application Priority Data

Sep. 3, 2008  (JP) .................... 2008-226396

(51) Int. Cl.
*G01N 33/00* (2006.01)
*G01N 35/00* (2006.01)

(52) U.S. Cl.
CPC ............ *G01N 35/00663* (2013.01); *G01N 2035/00673* (2013.01)

(58) Field of Classification Search
None
See application file for complete search history.

(56) References Cited

U.S. PATENT DOCUMENTS

| 5,719,059 A * | 2/1998 | Mimura et al. ............ 436/50 |
| 6,544,476 B1 * | 4/2003 | Mimura et al. ............ 422/67 |
| 2002/0107642 A1 * | 8/2002 | Nishida ............ G01N 35/00663 702/23 |
| 2004/0102997 A1 * | 5/2004 | Kikuchi ............ G01N 35/00663 422/62 |
| 2005/0154919 A1 * | 7/2005 | Noguchi et al. ............ 713/201 |
| 2005/0170356 A1 * | 8/2005 | Kureshy et al. ............ 435/6 |
| 2006/0064270 A1 * | 3/2006 | Onomichi ........ G01N 35/00594 702/119 |
| 2006/0148063 A1 | 7/2006 | Fauzzi et al. |

(Continued)

FOREIGN PATENT DOCUMENTS

| EP | 0 952 452 A1 | 10/1999 |
| JP | 1-250758 | 10/1989 |

(Continued)

OTHER PUBLICATIONS

Extended European Search Report issued Sep. 16, 2011 in Patent Application No. 09011227.7.

(Continued)

*Primary Examiner* — Jill Warden
*Assistant Examiner* — Benjamin R Whatley
(74) *Attorney, Agent, or Firm* — Oblon, McClelland, Maier & Neustadt, L.L.P.

(57) ABSTRACT

In an automatic analyzing apparatus that analyzes a mixture of a tested sample and a reagent, by selecting the reagent, acquiring cross-check information unique to the kind of the selected reagent, inputting input information for acquiring permission for input of data including an analysis parameter of the selected reagent, and cross-checking the cross-check information and the input information, it is determined whether to permit the input of the data. In a case that it is determined to permit the input of the data, the input of the data is accepted and, based on the analysis parameter reflecting the inputted data, the mixture of the tested sample and the reagent is measured and analysis data is generated.

11 Claims, 14 Drawing Sheets

(56) References Cited

U.S. PATENT DOCUMENTS

| | | | |
|---|---|---|---|
| 2007/0053793 A1* | 3/2007 | Maeda | G01N 35/00594 422/63 |
| 2007/0217949 A1* | 9/2007 | Mimura | G01N 35/00603 422/63 |
| 2008/0063570 A1* | 3/2008 | Fujino | G01N 35/00663 422/400 |
| 2008/0169909 A1* | 7/2008 | Park et al. | 340/10.4 |
| 2008/0240984 A1* | 10/2008 | Wakamiya | G01N 35/00732 422/67 |
| 2008/0240991 A1* | 10/2008 | Wakamiya | G01N 35/00663 422/68.1 |
| 2009/0058617 A1* | 3/2009 | Wu et al. | 340/10.41 |
| 2009/0142231 A1* | 6/2009 | Shibuya | G01N 35/00663 422/68.1 |
| 2010/0042351 A1* | 2/2010 | Covey | G01N 15/1404 702/108 |

FOREIGN PATENT DOCUMENTS

| | | |
|---|---|---|
| JP | 2000-9735 | 1/2000 |
| JP | 3300704 | 4/2002 |
| JP | 2005-196508 | 7/2005 |
| JP | 2006-30100 | 2/2006 |
| JP | 2006-125918 | 5/2006 |
| JP | 2006-276040 | 10/2006 |
| JP | 2007-240224 | 9/2007 |

OTHER PUBLICATIONS

Office Action issued Feb. 6, 2015 in European Patent Application No. 09 011 227.7.

\* cited by examiner

FIG. 5

63 REAGENT INFORMATION DISPLAY SCREEN

| | ITEM | REAGENT | POSITION | EXPIRATION DATE | ID | MANUFACTURER | --- |
|---|------|---------|----------|-----------------|------|--------------|-----|
| 1 | AST  | AST I   | 1A1      | 08-12-05        | 1000 | A COMPANY    | --- |
| 2 | AST  | AST II  | 2A1      | 08-12-10        | 1001 | A COMPANY    | --- |
| 3 | TP   | TP I    | 1A2      | 09-03-06        | 1005 | B COMPANY    | --- |
| m | | | | | | | --- |

FIG. 7

65 ANALYZE PARAMETER SETTING SCREEN

| | | |
|---|---|---|
| ITEM | AST | ~651 |

| | | |
|---|---|---|
| SAMPLE AMOUNT | 5.0 | ~652 |

REAGENT

| | | | | | |
|---|---|---|---|---|---|
| FIRST REAGENT | AST I | 653 | FIRST REAGENT AMOUNT | 150 | 655 |
| SECOND REAGENT | AST II | 654 | SECOND REAGENT AMOUNT | 50 | 656 |

| | | | |
|---|---|---|---|
| WAVELENGTH | WAVELENGTH 1 | 340 ▼ | ~657 |
| | WAVELENGTH 2 | 380 ▼ | ~658 |

| | | | |
|---|---|---|---|
| PHOTOMETRIC POINT | 20 | ~ | 29 |
| | 659 | | 660 |

66 USER ACCOUNT REGISTRATION SCREEN

FIG. 13

68 REAGENT MANAGEMENT SCREEN

| | ITEM | REAGENT | POSITION | EXPIRATION DATE | ID | MANUFACTURER | --- |
|---|---|---|---|---|---|---|---|
| 1 | AST | AST I | 1A1 | 08-12-05 | 1000 | A COMPANY | --- |
| 2 | AST | AST II | 2A1 | 08-12-10 | 1001 | A COMPANY | --- |
| 3 | TP | TP I | 1A2 | 09-03-06 | 1005 | B COMPANY | --- |
| m | | | | | | | --- |

AUTOMATIC ANALYZING APPARATUS

BACKGROUND OF THE INVENTION

1. Field of the Invention

The present invention relates to an automatic analyzing apparatus that analyzes components contained in a sample, more specifically, relates to an automatic analyzing apparatus that analyzes components contained in body fluid such as blood and urine of human, by using reagents for the components.

2. Description of the Related Art

An automatic analyzing apparatus, for biochemical test items and immunoserological test items, measures change in color tone, etc., resulting from reaction of a mixture of a tested sample and a reagent for each test item, thereby generating analysis data represented by density values and enzyme activity values of various test item components in the tested sample. In a facility where the automatic analyzing apparatus is employed, in order to enable analysis by reagents for test items necessary for tests, analysis parameters such as the amount of a sample and the amount of a reagent are set for each of the test items, and each of the test items is analyzed based on the set analysis parameters.

In recent years, since the number of reagent containers for containing reagents has increased in accordance with increase of the kinds of analyzable test items, there arises a problem that when a reagent container being short of a reagent is removed and an unused reagent container is housed into the apparatus, the reagent container may be housed in a wrong position. To solve this problem, such an automatic analyzing apparatus is known that can select a correct reagent even if a reagent container is placed in any position, by a user's attachment of barcode labels corresponding to information of reagents to reagent containers and reading of the attached barcode labels with a barcode reader (refer to Japanese Patent No. 3300704).

An automatic analyzing apparatus is operated by various users.

Thus, for example, such an automatic analyzing apparatus is known that can set an operable range in a plurality of stages in accordance with the levels of users so as to prevent a user having insufficient knowledge from incorrectly operating and enable each of the users to operate in consistent with the level of the user (refer to Japanese Unexamined Patent Publication No. 1-250758).

The users of this automatic analyzing apparatus are classified into, for example, high-level users acquainted with all the operations, middle-level users capable of executing necessary operations with no difficulty, and low-level users unfamiliar with the operations. For example, regarding analysis parameters in four kinds of functions, only a high-level user is permitted to operate all the functions, such as reading, writing and changing, of the contents of the analysis parameters. A middle-level user is permitted to operate only part of the functions, and a low-level user is limited in operation.

As a result of this classification, for example, high-level users select users having knowledge about analysis parameters of each test item, and the middle-level users usually perform the operations of the automatic analyzing apparatus in daily tests.

However, the middle-level users are not classified only by considering analysis parameters of each test item. Therefore, when there are many kinds of test items, the middle-level users may be permitted to operate analysis parameters of an unfamiliar test item. In this case, if the operation is incorrectly performed and the analysis parameters are not correctly set or changed, abnormal analysis data may be generated due to incorrect analysis.

SUMMARY OF THE INVENTION

The present invention was made in order to solve the above problem. An object of the present invention is to provide an automatic analyzing apparatus that is configured to correctly set or change analysis parameters to prevent incorrect analysis.

In order to achieve the above object, in an aspect of an automatic analyzing apparatus of the present invention, the automatic analyzing apparatus analyzes a mixture of a tested sample and a reagent, and comprises: a selecting part configured to select the reagent; an acquiring part configured to acquire cross-check information unique to the kind of the reagent selected by the selecting part; a permission input part configured to input information for obtaining permission for input of data including an analysis parameter of the reagent selected by the selecting part; a determining part configured to determine whether to permit the input of the data by cross-checking the cross-check information and the input information; and a measuring part configured to accept the input of the data when the determining part determines to permit the input of the data and, based on the analysis parameter reflecting the inputted data, measure the mixture of the tested sample and the reagent, thereby generating analysis data.

By thus configuration, when a password being the cross-check information of a reagent for identifying the reagent and a password being the input information associated therewith coincide, it is possible to set or change the analysis parameter of a test item relating to the reagent password. Consequently, it becomes possible to prevent incorrect setting and change of an analysis parameter, and it is possible to precisely analyze each test item.

BRIEF DESCRIPTION OF THE DRAWINGS

FIG. 5 shows an example of a reagent information display screen displayed on a display according to the embodiment of the present invention.

FIG. 7 shows an example of an analysis parameter setting screen displayed on the display according to the embodiment of the present invention.

FIG. 13 is a view showing an example of a reagent management screen displayed on the display according to the embodiment of the present invention.

DETAILED DESCRIPTION OF THE EMBODIMENTS

An embodiment of an automatic analyzing apparatus according to the present invention will be described below with reference to FIGS. 1 through 14.

Figure 1:
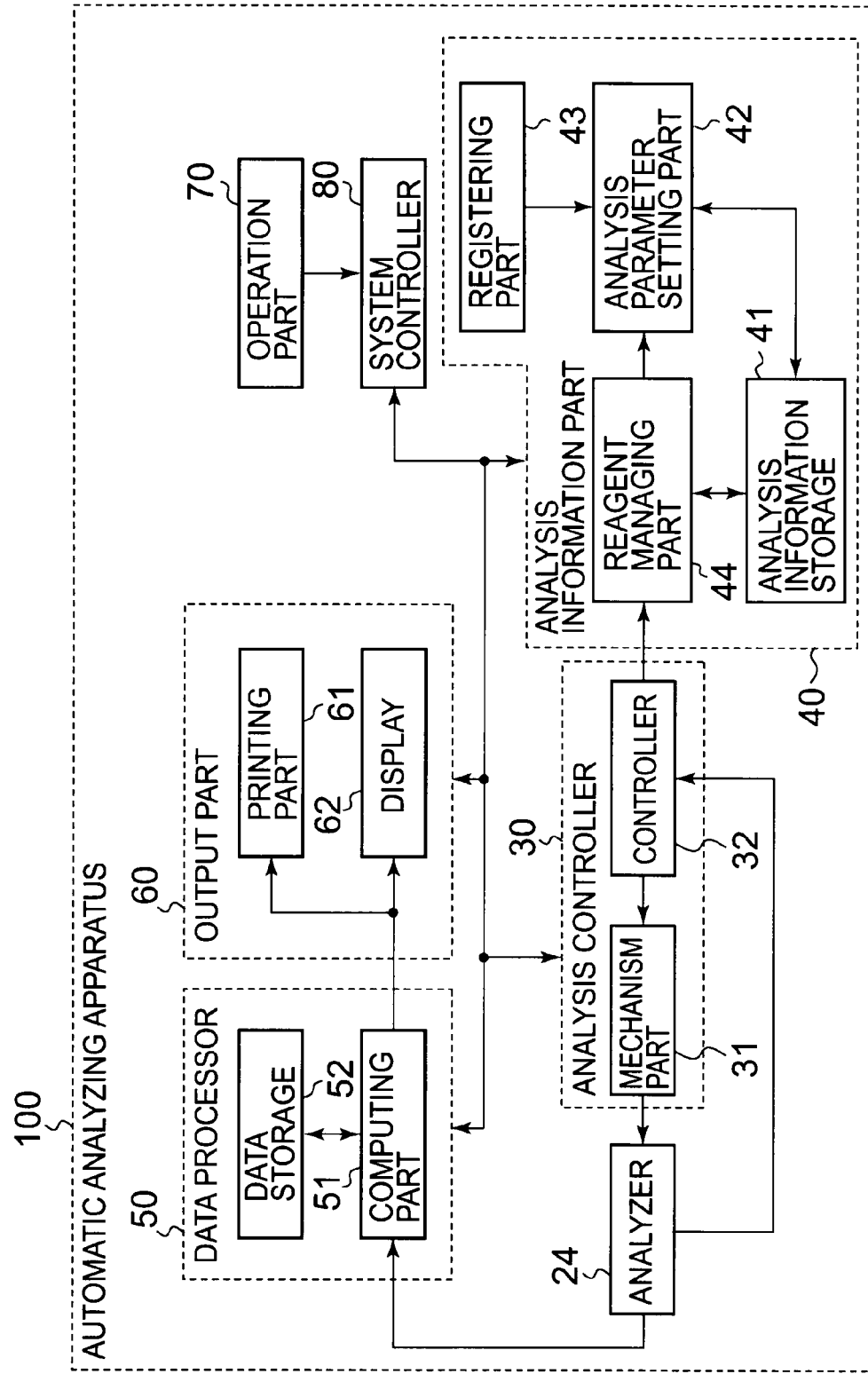
FIG. 1 is a block diagram showing the configuration of an automatic analyzing apparatus according to an embodiment of the present invention.

FIG. 1 is a block diagram showing the configuration of an automatic analyzing apparatus according to the embodiment of the present invention. An automatic analyzing apparatus 100 is provided with: an analyzer 24 configured to measure a mixture of a sample such as a standard sample of each test item and/or a tested sample collected from a subject with a reagent for each test item, and generate a standard signal and/or a tested signal; an analysis controller 30 configured to control the analyzer 24; and an analysis information part 40 configured to store reagent information for identifying a reagent for a test item analyzable by the automatic analyzing apparatus 100 and store analysis parameters for enabling analysis relating to the reagent information.

The analysis parameters are the amount of a sample, the amount of a reagent necessary for measurement, etc.

Further, the automatic analyzing apparatus 100 is provided with: a data processor 50 configured to process the standard signal and/or tested signal generated by the analyzer 24 and generate calibration data and/or analysis data; an output part 60 configured to output the calibration data and/or analysis data generated by the data processor 50; an operation part 70 for inputting various kinds of command signals; and a system controller 80 configured to integrally control the analysis controller 30, the analysis information part 40, the data processor 50, and the output part 60.

Figure 2:
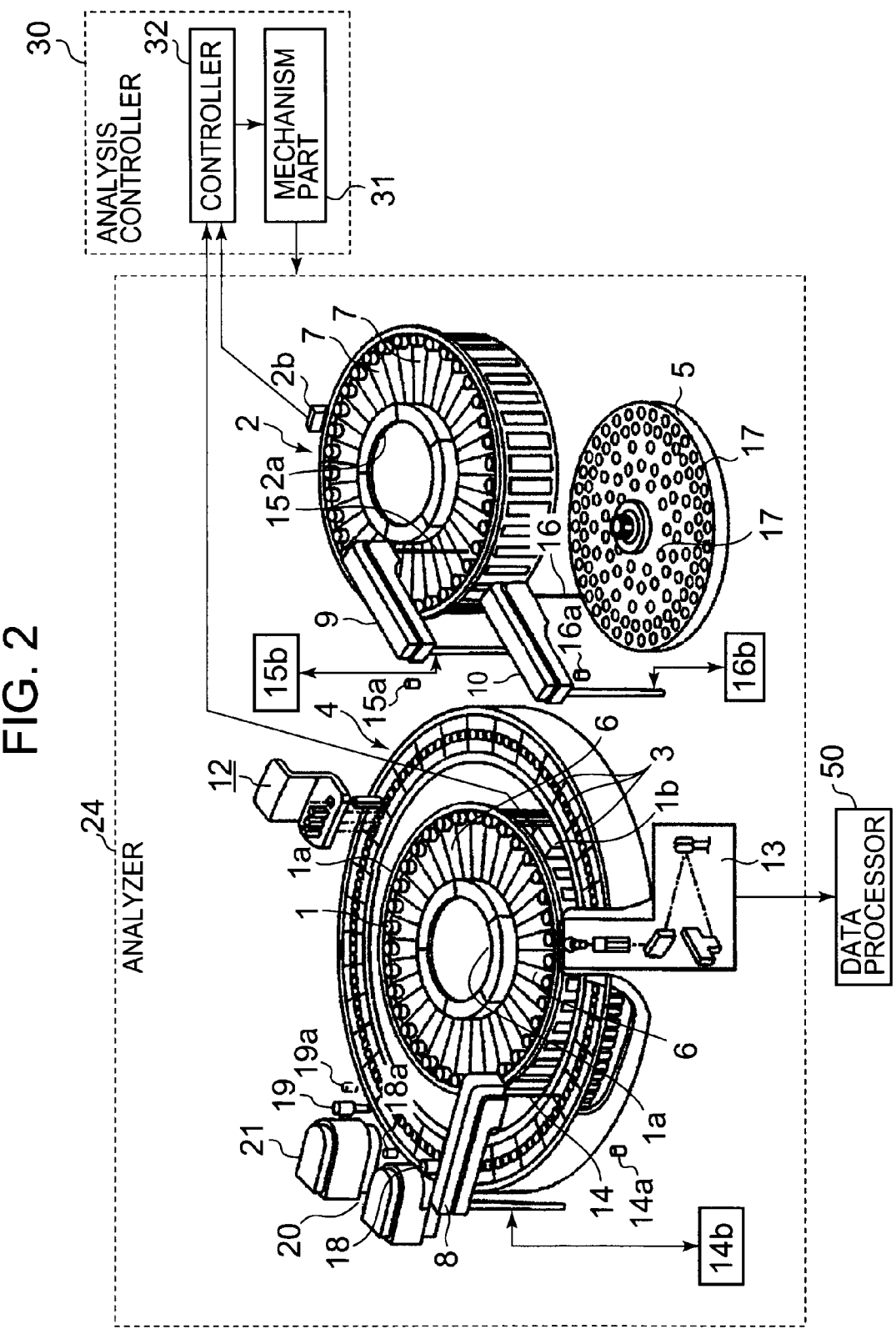
FIG. 2 is a perspective view showing the configuration of an analyzer according to the embodiment of the present invention.

FIG. 2 is a perspective view showing the configuration of the analyzer 24. The analyzer 24 is provided with a disk sampler 5 configured to rotatably hold a sample container 17 containing a sample such as a standard sample and a tested sample; a reagent container 6 configured to contain a first reagent of one-reagent system or two-reagent system that reacts with a test item component contained in the sample; and a first reagent storage 1 that has a rack 1a rotatably holding the reagent container 6 and a reader 1b. The reader 1b is configured to read first reagent information for identifying the first reagent written on the reagent container 6 held by the rack 1a.

Further, the analyzer 24 is provided with: a reagent container 7 configured to contain a second reagent paired with the first reagent of two-reagent system; a second reagent storage 2 having a rack 2a rotatably holding the reagent container 7 and a reader 2b; and a reaction disk 4 configured to rotatably hold a plurality of reaction containers 3 placed on the circumference. The reader 2b is configured to read second reagent information for identifying a second reagent written on the reagent container 7 held by the rack 2a. The first reagent information and the second reagent information read by the readers 1b and 2b of the first and second reagent storages 1 and 2 are outputted to the analysis controller 30.

Further, the analyzer 24 is provided with: a sample dispensing pump 16b configured to perform a dispensing operation of sucking the sample in the sample container 17 held by the disk sampler 5 into a sample dispensing probe 16 and discharging the sample into the reaction container 3; a cleaning tank 16a configured to clean the sample dispensing probe 16 every time the operation of dispensing the sample ends; and a sample dispensing arm 10 configured to hold the sample dispensing probe 16 so as to be rotatable and vertically movable in order to perform the operation of dispensing the sample.

Further, the analyzer 24 is provided with: a first reagent dispensing pump 14b configured to perform a dispensing operation of sucking the first reagent in the reagent container 6 held by the reagent storage 1 into a first reagent dispensing probe 14 and discharging the first reagent into the reaction container 3 in which the sample has been dispensed; a cleaning tank 14a configured to clean the first reagent dispensing probe 14 every time the operation of dispensing the first reagent ends; and a first reagent dispensing arm 8 configured to hold the first reagent dispensing probe 14 so as to be rotatable and vertically movable in order to perform the operation of dispensing the first reagent.

Further, the analyzer 24 is provided with: a first stirring part 18 for stirring a first mixture composed of the sample and the first reagent dispensed into the reaction container 3; a cleaning tank 18a configured to clean the first stirring part 18 every time the stir of the first mixture ends; and a first stirring arm 20 configured to hold the first stirring part 18 so as to be rotatable and vertically movable.

Further, the analyzer 24 is provided with: a second reagent dispensing pump 15b configured to perform a dispensing operation of sucking the second reagent in the reagent container 7 held by the reagent storage 2 into a second reagent dispensing probe 15 and discharging the second reagent into the reaction container 3 in which the sample and the first reagent have been dispensed; a cleaning tank 15a configured to clean the second reagent dispensing probe 15 every time the operation of dispensing the second reagent ends; and a second reagent dispensing arm 9 configured to hold the second reagent dispensing probe 15 so as to be rotatable and vertically movable in order to perform the operation of dispensing the second reagent.

Further, the analyzer 24 is provided with: a second stirring part 19 for stirring a second mixture composed of the sample, the first reagent, and the second reagent that have been dispensed into the reaction container 3; a cleaning tank 19a configured to clean the second stirring part 19 every time the stir of the second mixture ends; a second stirring arm 21 configured to hold the second stirring part 19 so as to be rotatable and vertically movable; a photometric unit 13 configured to optically measure the first mixture and the second mixture in the reaction container 3; and a cleaning unit 12 that have a sucking nozzle for sucking the first mixture and the second mixture after the measurement in the reaction container 3, a cleaning nozzle for cleaning the inside of the reaction container 3 after the suck of the first mixture and the second mixture, and a drying nozzle for drying the inside of the reaction container 3 after the cleaning.

The photometric unit 13 applies light to the first mixture or second mixture including the standard sample within the reaction container 3 rotationally moving, and generates a standard signal by detecting the wavelength light of a test item transmitted through the mixture and converting it into an electric signal. Moreover, the photometric unit 13 applies light to the first mixture or the second mixture including the tested sample within the reaction container 3, and generates a tested signal by detecting the wavelength of a test item transmitted through the mixture and converting it into an electric signal.

Then, the photometric unit 13 outputs the generated standard signal and tested signal to the data processor 50. Moreover, the reaction container 3 after the measurement is cleaned and dried, and thereafter used for the measurement again.

Figure 3:
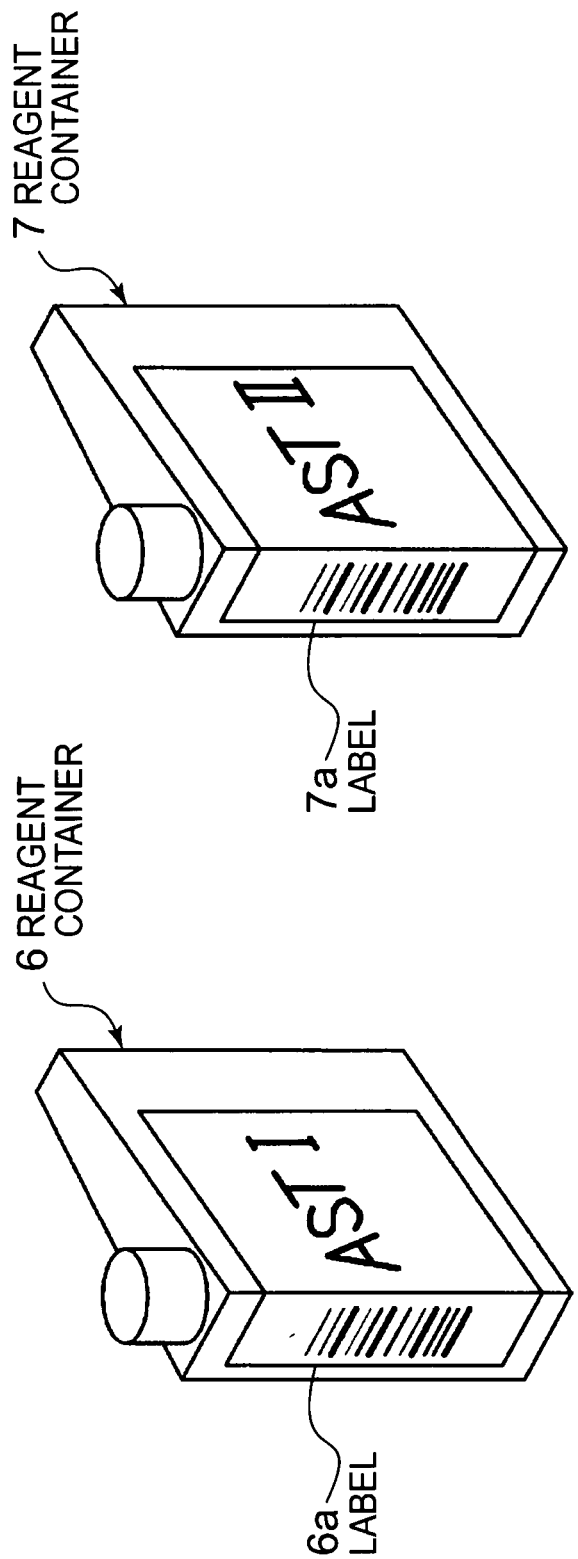
FIG. 3 shows the appearance of reagent containers housed into first and second reagent storages of the analyzer according to the embodiment of the present invention.

FIG. 3 shows the appearance of the reaction containers 6 and 7 held by the first and second reagent storages 1 and 2 of the analyzer 24.

The first reagent information and the second reagent information, such as a label 6a and a label 7a displayed by one-dimensional or two-dimensional code, for identifying the first and second reagents in the reagent containers 6 and 7 are attached.

The first reagent information of one-reagent system includes a reagent ID for identifying the first reagent in the reagent container 6, the name of a test item of the first reagent, a first reagent password for enabling the setting or change of analysis parameters of the test item and also for identifying the first reagent, the name of the first reagent, the expiration date of the first reagent, information of a manufacturer or a distributer of the first reagent, the lot number of the first reagent, etc.

Further, the first reagent information of two-reagent system includes a reagent ID for identifying the first reagent in the reagent container 6, the name of a test item of the first reagent, a first reagent password for enabling the setting or change of analysis parameters of the test item and also for identifying the first reagent, the name of the first reagent, the expiration date of the first reagent, the lot number of the first reagent, etc. Moreover, the second reagent information includes a reagent ID for identifying the second reagent in the reagent container 7, the name of the test item of the second reagent, which is the same as the name of the test item of the first reagent, a second reagent password for enabling the setting or change of analysis parameters of the test item and also for identifying the second reagent, the name of the second reagent, the expiration date of the second reagent, the lot number of the second reagent, etc. Furthermore, as reagent information common to the first reagent information and the second reagent information of the two-reagent system, information of the manufacturer or distributor of the first and second reagents, etc., are included.

The analysis controller 30 of FIG. 1 is provided with a mechanism part 31 having a mechanism for driving each analysis unit of the analyzer 24, and a controller 32 for controlling each mechanism of the mechanism part 31 to actuate each analysis unit of the analyzer 24.

The mechanism part 31 is provided with a mechanism configured to respectively rotate the rack 1a of the reagent storage 1, the rack 2a of the second reagent storage 2 and the disk sampler 5, a mechanism configured to rotate the reaction disk 4, a mechanism configured to respectively rotate and vertically move the sample dispensing arm 10, the first reagent dispensing arm 8, the second reagent dispensing arm 9, the first stirring arm 20 and the second stirring arm 21, and a mechanism configured to vertically move the cleaning unit 12, in the analyzer 24.

Further, the mechanism part 31 is provided with: a mechanism configured to respectively drive the sample dispensing pump 16b, the first reagent dispensing pump 14b and the second reagent dispensing pump 15b to suck and discharge; a mechanism configured to respectively drive the first stirring part 18 and the second stirring part 19 to stir; a mechanism configured to drive, so as to suck, a sucking pump that sucks into the sucking nozzle of the cleaning unit 12; a mechanism configured to drive a cleaning pump that causes the cleaning nozzle to discharge and suck a cleaning agent to suck and discharge; a mechanism configured to drive, so as to dry, a drying pump that causes the drying nozzle to dry; etc.

The controller 32 is provided with a control circuit that controls the respective mechanisms of the mechanism part 31. Moreover, the controller 32 outputs, to the analysis information part 40, first reagent information and second reagent information obtained by adding, to the first reagent information and second reagent information outputted from the readers 1b and 2b of the analyzer 24, information of the housing positions of the first and second reagent storages 1 and 2 in which the reagent containers 6 and 7 having the first reagent information and second reagent information are housed.

The analysis information part 40 is provided with: an analysis information storage 41 that can store the first or second reagent information for identifying the first or second reagent for each test item analyzable by the automatic analyzing apparatus 100 in association with analysis parameters of a test item analyzable by using a reagent identified by the reagent information; an analysis parameter setting part 42 that stores analysis parameters of each test item analyzable by the automatic analyzing apparatus 100 into the analysis information storage 41; a registering part 43 that registers and stores a user account of a user authorized to access the automatic analyzing apparatus 100; and a reagent managing part 44 that stores the first reagent information and the second reagent information outputted from the controller 32 of the analysis controller 30, into the analysis information storage 41.

The analysis parameter setting part 42 stores analysis parameters supplied from the system controller 80 in response to an input operation of setting the analysis parameters via the operation part 70, into the analysis information storage 41 in association with the first reagent information of the one-reagent system and the first and second reagent information of the two-reagent system relating to the analysis parameters.

Further, the analysis parameter setting part 42 changes the analysis parameters stored in the analysis information storage 41, to analysis parameters supplied from the system controller 80 in response to an input operation of changing the analysis parameters via the operation part 70, and stores the analysis parameters. Furthermore, the analysis parameter setting part 42 reads out and outputs the analysis parameters stored in the analysis information storage 41 to the output part 60.

The registering part 43, in response to an input operation of registering a user account of a user to be authorized to access the automatic analyzing apparatus 100, registers and stores the user account supplied from the system controller 80 and information of a previously set operable range in the automatic analyzing apparatus 100 associated with the user account.

The reagent managing part 44 stores the first reagent information of one-reagent system and the first and second reagent information of two-reagent system outputted from the controller 32, into the analysis information storage 41. Moreover, the reagent managing part 44 outputs, to the output part 60, reagent information obtained by excluding the first and second reagent passwords from the first reagent information of one-reagent system and the first and second reagent information of two-reagent system stored in the analysis information storage 41.

Furthermore, the reagent managing part 44 outputs, to the output part 60, reagent information obtained by excluding the first and second reagent passwords from the first reagent information of one-reagent system and the first and second reagent information of two-reagent system outputted from the controller 32.

The data processor 50 is provided with: a computing part 51 configured to process a standard signal and a tested signal outputted from the photometric unit 13 of the analyzer 24 and generate calibration data and analysis data of each test item; and a data storage 52 configured to store the calibration data and the analysis data generated by the computing part 51.

The computing part 51 generates, from the standard signal outputted from the photometric unit 13 and a standard value of a standard sample previously set, calibration data representing the relation between the density value or activity value of a component of each test item and the standard signal, and outputs the generated calibration data to the output part 60 and also stores it into the data storage 52.

Further, the computing part 51 reads out calibration data of a test item corresponding to the tested signal outputted from the photometric unit 13, from the data storage 52. Next, the computing part 51 generates analysis data represented as the density value or activity value from the tested signal by using the read-out calibration data, and outputs the generated analysis data to the output part 60 and also stores it into the data storage 52.

The data storage 52 is provided with a hard disk, etc., and stores the calibration data outputted from the computing part 51 for each test item. Moreover, the data storage 52 stores the analysis data of each test item outputted from the computing part 51, for each tested sample.

The output part 60 is provided with: a printing part 61 configured to print out the calibration data and analysis data outputted from the computing part 51 of the data processor 50; and a display 62 configured to display the aforementioned data. The printing part 61 is provided with a printer, etc., and prints out the calibration data and analysis data outputted from the computing part 51 to a printing sheet in a previously set format.

The display 62 is provided with a monitor such as a CRT and a liquid crystal panel, and displays the calibration data and analysis data outputted from the computing part 51. Moreover, the display 62 displays: a reagent information display screen or a reagent management screen that displays the first reagent information and the second reagent information; a reagent logon screen for inputting the first or second reagent password that enables the setting or change of analysis parameters of each test item; an analysis parameter setting screen for setting or changing the analysis parameters of each test item; a user account registration screen for registering a user account of a user authorized to access the automatic analyzing apparatus 100; a user logon screen for inputting the registered user account; etc.

The operation part 70 is provided with an input device such as a keyboard, a mouse, a button and a touch panel, and performs an operation of inputting various command signals, an operation of displaying the reagent information display screen and the reagent management screen, an operation of displaying the reagent logon screen, a reagent logon operation of inputting the first or second reagent password to enable the setting or change of the analysis parameters, an input operation of setting or changing the analysis parameters, an operation of displaying the user account registration screen, an input operation of registering the user account, a user logon operation of inputting the registered user account and making the automatic analyzing apparatus 100 operable, etc.

The system controller 80 is provided with a CPU and a memory circuit, and stores information such as command signals, user accounts, analysis parameters, the first reagent password and the second reagent password supplied by the operation via the operation part 70. Then, based on the supplied information, the system controller 80 executes control of the whole system such as control of the respective units of the analyzer 24 to operate at a constant analysis cycle.

Figure 4:
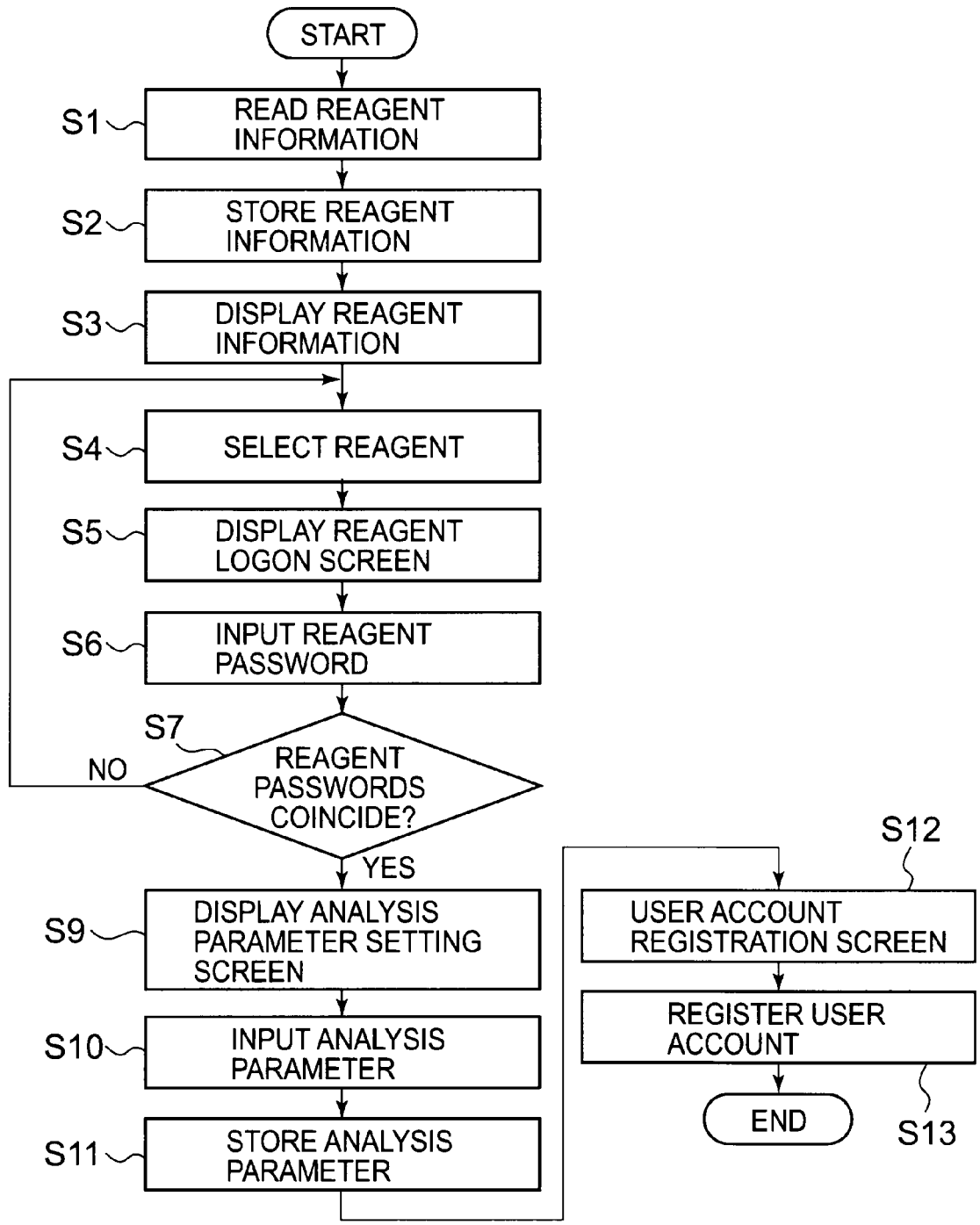
FIG. 4 is a flowchart showing the operation of the automatic analyzing apparatus in response to a reagent logon operation and an input operation for registering a user account.
Figure 6:
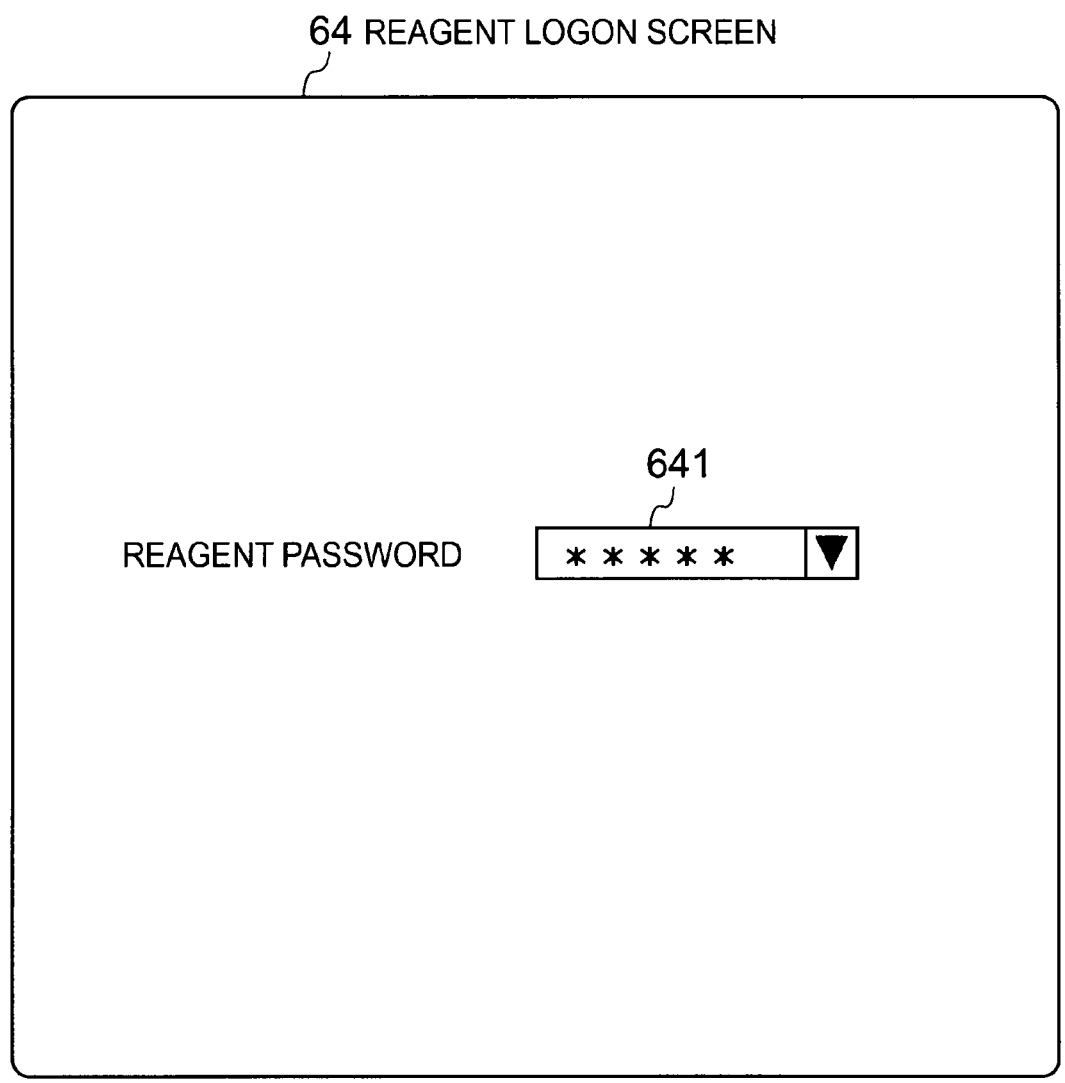
FIG. 6 shows an example of a reagent logon screen displayed on the display for setting analysis parameters according to the embodiment of the present invention.
Figure 8:
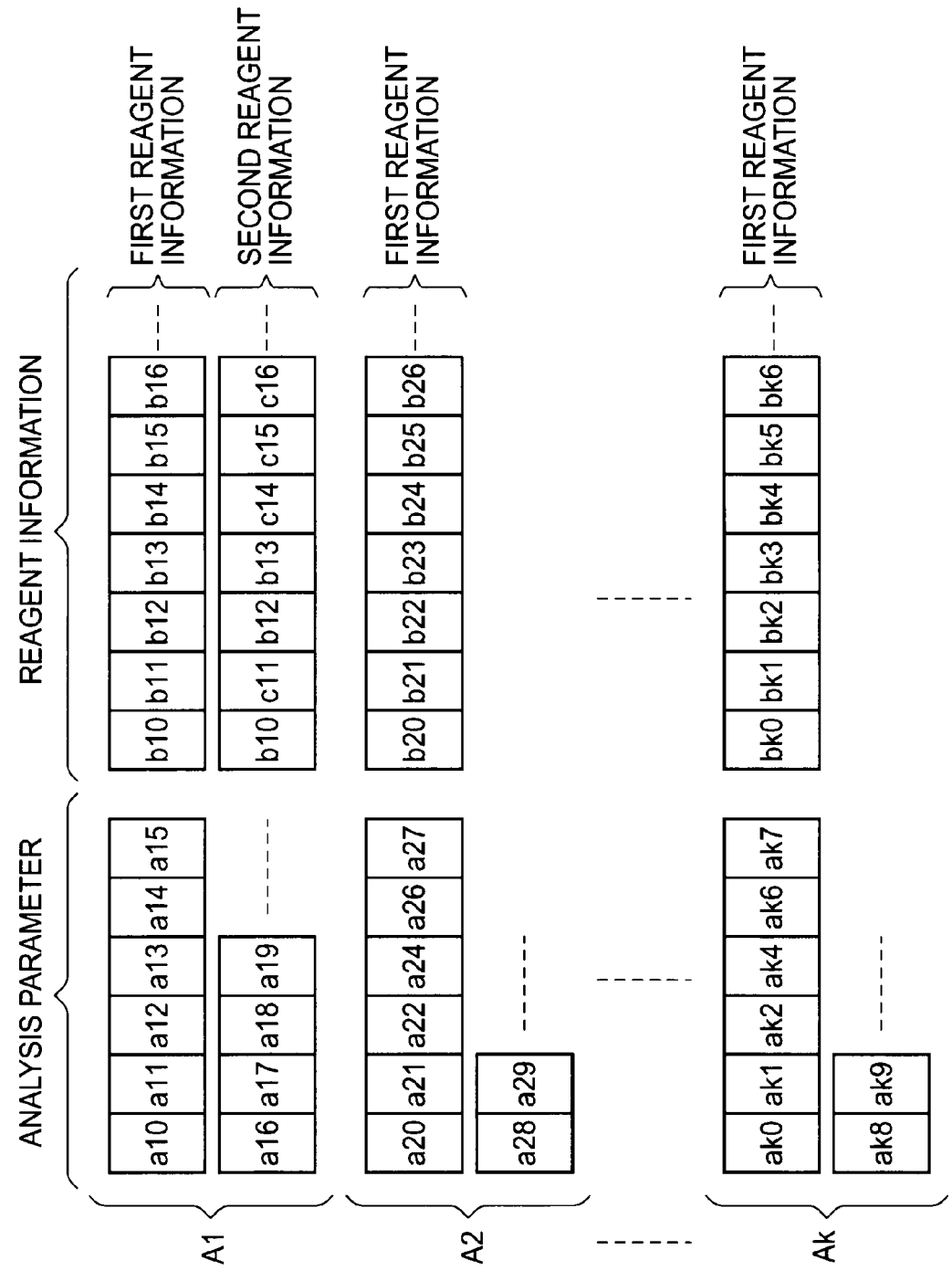
FIG. 8 shows an example of analysis information stored in an analysis information storage according to the embodiment of the present invention.

With reference to FIGS. 1 through 13, an example of the operation of the automatic analyzing apparatus 100 will be described below. FIG. 4 is a flowchart showing the operation of the automatic analyzing apparatus 100 in response to the reagent logon operation and the input operation of registering a user account. FIG. 5 is a view showing an example of the reagent information display screen displayed on the display 62. FIG. 6 is a view showing an example of the reagent logon screen displayed on the display 62 for setting analysis parameters. FIG. 7 is a view showing an example of the analysis parameter setting screen displayed on the display 62. FIG. 8 is a view showing an example of analysis information stored in the analysis information storage 41.

Figure 9:
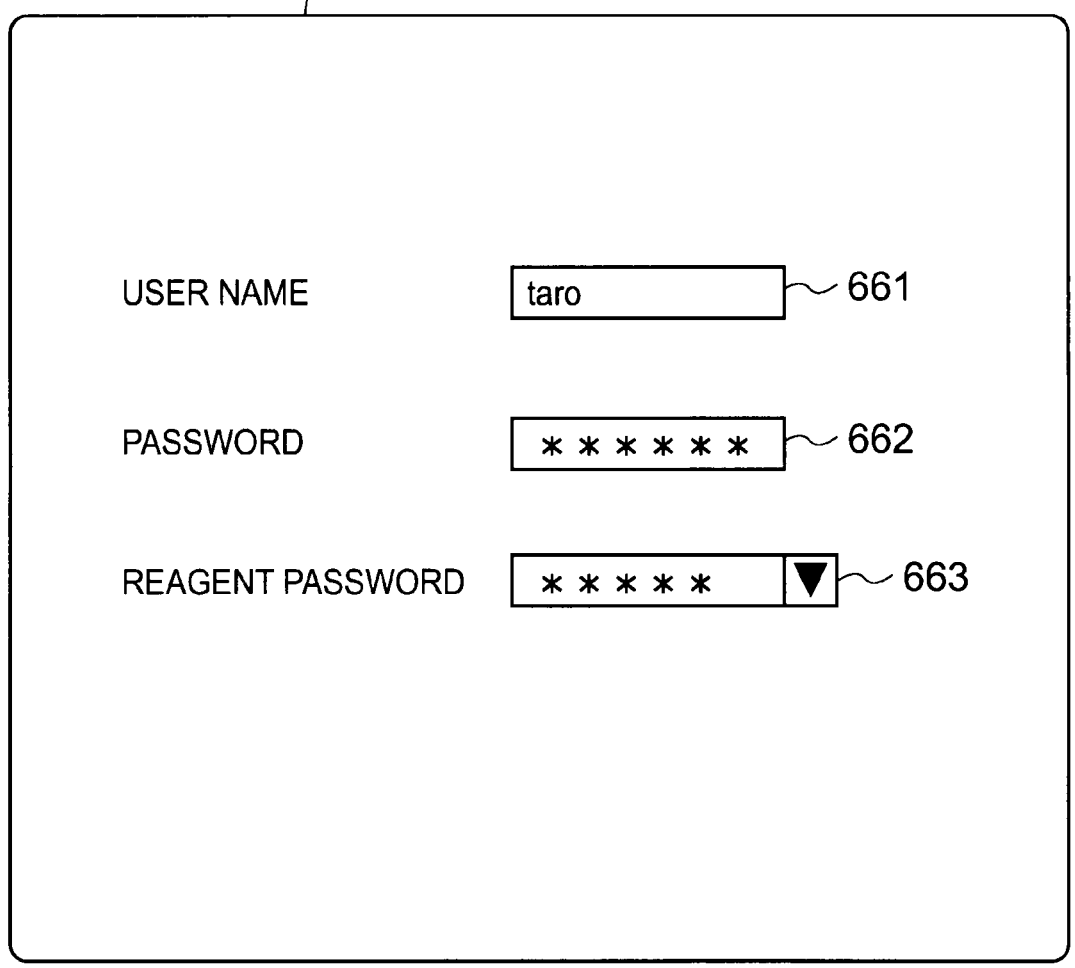
FIG. 9 shows an example of a user account registration screen displayed on the display according to the embodiment of the present invention.
Figure 10:
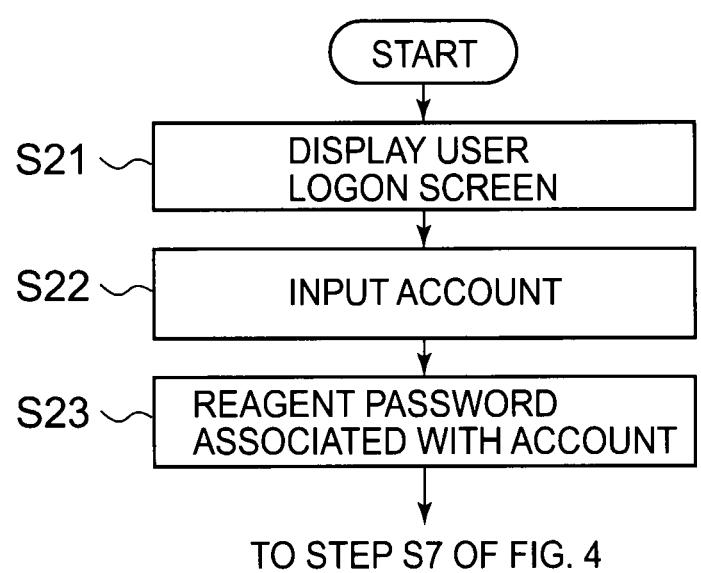
FIG. 10 is a flowchart showing the operation of the user logon operation according to the embodiment of the present invention.
Figure 11:
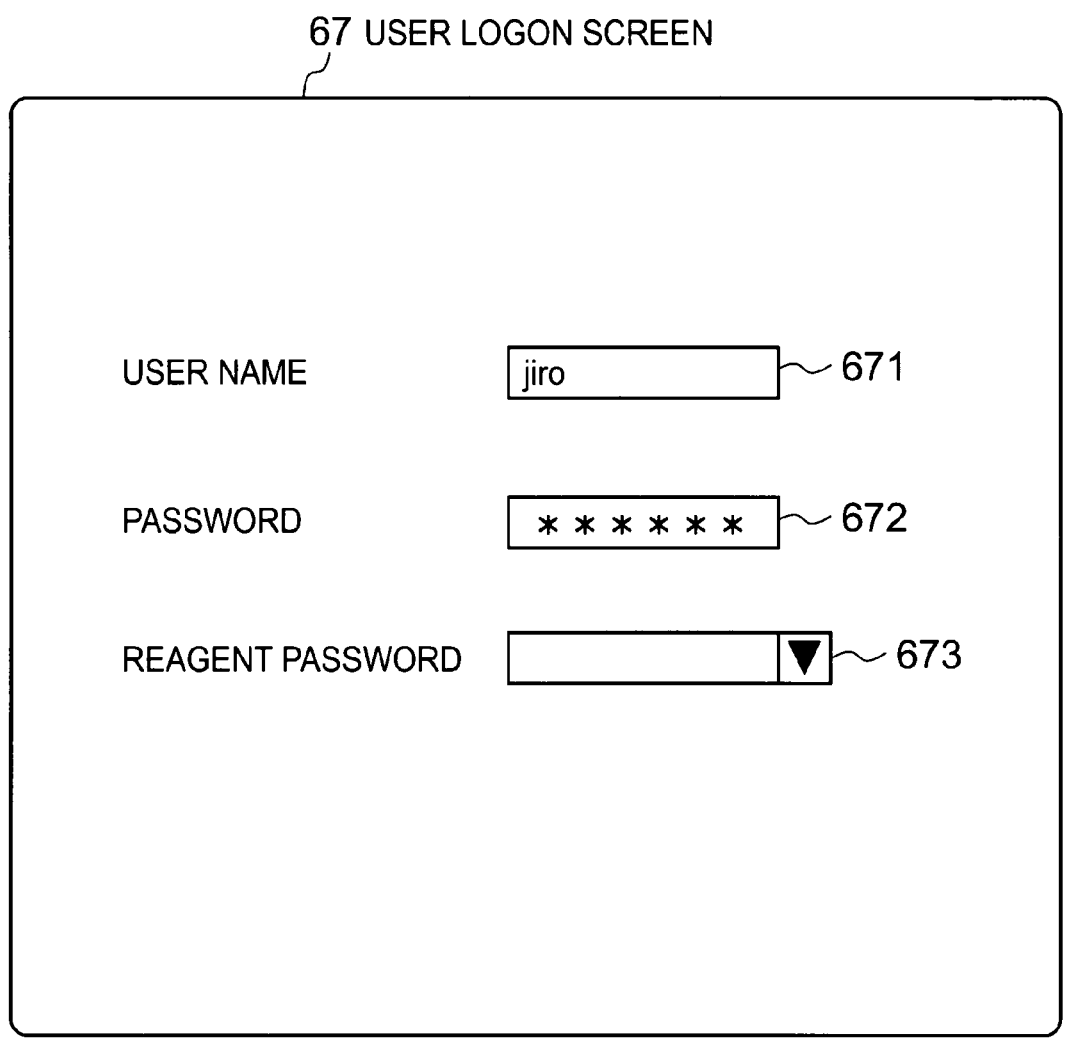
FIG. 11 shows an example of a user logon screen displayed on the display according to the embodiment of the present invention.
Figure 12:
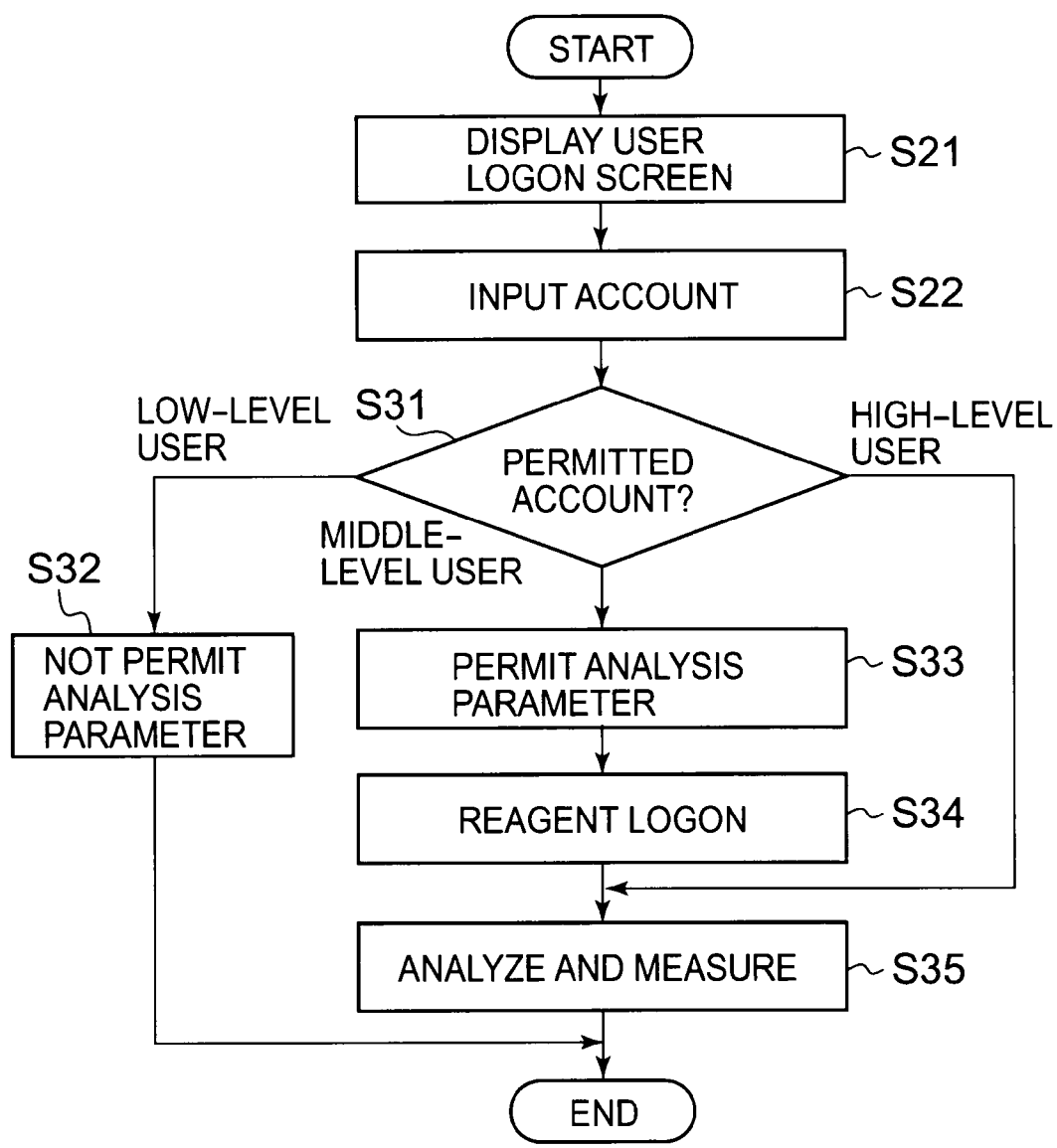
FIG. 12 is a flowchart showing the operation of the automatic analyzing apparatus corresponding to the user logon operation according to the embodiment of the present invention.

Further, FIG. 9 is a view showing an example of the user account registration screen displayed on the display 62. FIG. 10 is a flowchart showing the user logon operation and the operation of the automatic analyzing apparatus 100 in response to the user logon operation. FIG. 11 is a view showing an example of the user logon screen displayed on the display 62. FIG. 12 is a view showing an example of the reagent management screen displayed on the display 62. FIG. 13 is a view showing the reagent logon screen displayed on the display 62 for changing the analysis parameters.

In FIG. 4, the operation manager of the automatic analyzing apparatus 100 is experienced in all the operations of the automatic analyzing apparatus 100 including how to handle the analysis parameters of the respective analyzable test items, and has the first and second reagent passwords of reagents corresponding to analyzable test items. The operation manager executes the setting of the analysis parameters of the respective analyzable test items.

The reagent container 6 containing the first reagent and the reagent container 7 containing the second reagent of each test item analyzable in the automatic analyzing apparatus 100 are housed into the first and second reagent storages 1 and 2 of the analyzer 24. Then, when an operation of identifying the reagents housed in the first and second reagent storages 1 and 2 is executed via the operation part 70, the automatic analyzing apparatus 100 starts operation.

The system controller 80 instructs the analysis controller 30 and the analysis information part 40 to collect the reagent information. The controller 32 of the analysis controller 30 controls the mechanism part 31 to activate the racks 1a and 2a and the readers 1b and 2b of the first and second reagent storages 1 and 2.

The readers 1b and 2b read the first and second reagent information from the labels 6a and 7a attached to the reagent containers 6 and 7 held by the rotating racks 1a and 2a, and outputs to the controller 32 (step S1). The labels 6a and 7a are described with barcodes as shown in FIG. 3. By reading the barcodes, cross-check information is acquired. The controller 32 adds, to the first and second reagent information outputted from the readers 1b and 2b, information of the housing positions of the first and second reagent storages 1 and 2 housing the reagent containers 6 and 7 having the first and second reagent information, and outputs to the reagent managing part 44 of the analysis information part 40. The reagent managing part 44 stores the first and second reagent information outputted from the controller 32, into the analysis information storage 41 (step S2).

The reagent information to be read includes information indicating the property of a reagent. The information indicating the property of a reagent will be described later. Moreover, the reagent information to be read may include information that specifies the kind of a reagent as described above. On the other hand, the reagent information includes cross-check information unique to the specified reagent kind. That is to say, the cross-check information for determining permission for input of data is prepared uniquely to the kind of each reagent. Even to an operator among operators of the same level, the cross-check information differentiates the discrimination between a reagent for which data input is permitted and a reagent for which data input is not permitted, depending on whether the operator can input the input information conforming to the cross-check information.

The cross-check information may be a password. An example of the cross-check information being a password will be described later, together with the input information. Alternatively, the cross-check information may be another type of encoded information. In this case, it is possible to acquire the cross-check information by reading and decoding the encoded information. Although acquisition of the cross-check information from the reagent information having been read has been explained above, the cross-check information may be acquired from information inputted from the system controller 80 via the operation part 70 and registered. In this case, since all the operators are not permitted to register the cross-check information, the cross-check information is registered by the operation manager. This registering process will be described later with reference to FIG. 14.

When an operation of displaying the reagent information display screen is performed via the operation part 70 to confirm the first and second reagents housed in the first and second reagent storages 1 and 2 after the reagent information is read and stored, the reagent managing part 44 causes the display 62 to display the reagent information display screen to display the reagent information in which the first and second reagent passwords are excluded from the first and second reagent information stored in the analysis information storage 41 (step S3).

FIG. 5 is a view showing an example of the reagent information display screen displayed on the display 62. A reagent information display screen 63 is formed by fields of sequential numbers "1" through "m" and fields of "item," "reagent," "position," "expiration date," "ID," "manufacturer," etc., that respectively correspond to the fields "1" through "m." An example of the first and second reagent information displayed in the fields "1" through "3" will be described below.

For example, "AST" of a test item name is displayed in the "item" field corresponding to the field "1," and "AST I" of the name of a first reagent of two-reagent system in "AST" displayed in the "item" field is displayed in the "reagent" field. Moreover, "1A1" of a housing position of the first reagent storage 1 housing the reagent container 6 of "AST I" displayed in the "reagent" field is displayed in the "position" field, and "08-12-05" of the expiration date of "AST I" displayed in the "reagent" field is displayed in the "expiration date" field. Furthermore, "1000" of a reagent ID of "AST I" displayed in the "reagent" field is displayed in the "ID" field, and "A Company" of a manufacturer or distributor of "AST I" displayed in the "reagent" field is displayed in the "manufacturer" field.

"AST" of the same test item name as displayed in the "item" field of the field "1" is displayed in the "item" field corresponding to the field "2" corresponding to the field "2" and "AST II" of a second reagent name paired with "AST I" displayed in the "reagent" field of the field "1" is displayed in the "reagent" field. Moreover, "2A1" of a housing position of the second reagent storage 2 housing the reagent container 7 of "AST II" displayed in the "reagent" field is displayed in the "position" field, and "08-12-10" of the expiration date of "AST II" displayed in the "reagent" field is displayed in the "expiration date" field. Furthermore, "1001" of a reagent ID of "AST II" displayed in the "reagent" field is displayed in the "ID" field, and "A Company" of a manufacturer or distributor of "AST II" displayed in the "reagent" field is displayed in the "manufacturer" field.

"TP" of a test item name is displayed in the "item" field corresponding to the field "3," and "TP I" of the name of a first reagent of one-reagent system reagent in "TP" displayed in the "item" field is displayed in the "reagent" field. Moreover, "1A2" of a housing position of the first reagent storages 1 housing the reagent container 6 of "TP I" displayed in the "reagent" field is displayed in the "position" field, and "09-03-06" of the expiration date of "TP I" displayed in the "reagent" field is displayed in the "expiration date" field. Furthermore, "1005" of a reagent ID of "TP I" displayed in the "reagent" field is displayed in the "ID" field, and "B Company" of a manufacturer or distributor of "TP I" displayed in the "reagent" field is displayed in the "manufacturer" field.

Thus, from the first and second reagent information displayed on the reagent information display screen 63 of the display 62, it is possible to confirm the first and second reagent information of the first and second reagents for each analyzable test item housed in the first and second reagent storages 1 and 2.

Next, the reagent is selected (step S4). This identifying operation is an operation of specifying the kind of the reagent contained in the housed reagent container 7. In this operation, a reagent name or symbol that specifies the housed reagent is inputted from the system controller 80 via the operation part 70. Alternatively, this operation may be an operation of notifying that the reagent container 7 is housed. In this case, by reading the reagent information described above, the type of the reagent is specified from the information contained in the reagent information.

After confirmation of the first and second reagent information of the first and second reagents housed in the first and second reagent storages 1 and 2, the reagent logon screen is displayed for inputting the first or second reagent password.

When an operation of displaying the reagent logon screen is performed via the operation part 70, the system controller 80 causes the display 62 to display the reagent logon screen (step S5 of FIG. 4).

FIG. 6 is a view showing an example of the reagent logon screen displayed on the display 62 to set analysis parameters. A reagent logon screen 64 is composed of a "reagent password" field into which a plurality of first or second reagent passwords can be inputted.

A reagent password is inputted from the system controller 80 via the operation part 70 by the user (step S6). For example, when a reagent logon operation of inputting the first or second reagent password of "AST" of the test item name displayed in the "item" field of the reagent information display screen 63 shown in FIG. 5 is performed, "***" masking the reagent password is displayed within a combo box 641**.

This reagent password is inputted uniquely to a specified reagent in that the logon screen is opened for the specified reagent. The reagent password is input information for obtaining permission for input of data in that it is used for cross-checking with the cross-check information as described later. Therefore, a password, which is an example of the input information, is inputted. Although it has been described above that the cross-check information is a password, it shall be a similar password to the input information described here. The input information does not need to be a password necessarily. For example, information that can specify a reagent may be read as a code by a memory card. In this case, the cross-check information shall also be acquired as data of a similar form as the input information.

Then, the input information (password) is cross-checked and it is determined whether the read reagent password coincides with the inputted reagent password (step S7). Thus, the read password, which is an example of the cross-check information, is cross-checked with the inputted password, which is an example of the input information, whereby permission for input of data regarding the specified reagent is determined as described later. The permission for the data input is permission for the setting or change of the analysis parameters, for example. It is determined by cross-checking the reagent passwords whether the setting or change of the analysis parameters as an example of the data input is permitted or unpermitted. The system controller 80 supplies the inputted reagent password to the analysis parameter setting part 42.

The cross-checking of the reagent passwords is performed in the following manner. The analysis parameter setting part 42 searches to determine whether the reagent password supplied from the system controller 80 is stored in the analysis information storage 41. In a case that the reagent password supplied from the system controller 80 is not stored in the analysis information storage 41 (step S7: No), a state that the analysis parameters cannot be set or changed is maintained.

Simultaneously, it is determined that the reagent password is inputted by error, and a message such as "Wrong reagent password" is displayed on the display 62. In other words, error is displayed and the process goes back to step S4 for repeating processing including selection of the reagent.

Further, in a case that the reagent password supplied from the system controller 80 is stored in the analysis information storage 41 (step S7: Yes), it is determined that the data input is permitted, and the change or setting of the analysis parameters is accepted. The reagent information including the reagent password is read out from the analysis information storage 41, and the analysis parameter setting screen relating to the reagent password, on which the analysis parameters can be set or changed, is displayed on the display 62 (step S9).

Next, on the displayed analysis parameter setting screen, in association with the specified reagent, input of the data including the analysis parameters of the reagent is accepted. Then, the inputted data is sent to the analyzer 24 and reflected on analysis. The setting of the analysis parameters will be described with reference to FIG. 7.

FIG. 7 is a view showing an example of the analysis parameter setting screen displayed on the display 62. An analysis parameter setting screen 65 is composed of fields of "item," "sample amount," "reagent," "wavelength," "photometric point," etc, which are intended for setting each analysis parameter. In association with the specified reagent, parameters relating to analysis of the reagent, namely, the sample amount, the wavelength and the photometric point are inputted as the analysis parameters, and set into the analyzer 24.

In the "item" field, the test item name having been set is displayed. Then, "AST," which is the test item name included in the first or second reagent information of the first or second reagent password inputted by the reagent logon operation is set, and "AST" is displayed within a dialogue box 651. When an input operation of changing the test item name is performed, the changed test item name is displayed in the dialogue box 651, and the changed test item name is stored into the analysis information storage 41.

When an input operation of setting, in the "sample amount" field, 5 μL as a dispensing amount of each sample dispensed into the reaction container 3 to analyze the test item displayed in the "item" field is performed, "5.0" is displayed within a dialogue box 652.

The "reagent" field is composed of fields of "first reagent" and "second reagent" for setting a reagent for the test item displayed in the "item" field, and fields of "first reagent amount" and "second reagent amount" for setting the amounts of the reagents set in the "first reagent" and "second reagent" fields to be dispensed into the reaction container 3.

Then, "AST I" of the first reagent name included in the first reagent information corresponding to the first or second reagent password inputted by the reagent logon operation is set in the "first reagent" field, and "AST I" is displayed within a dialogue box 653.

Moreover, "AST II" of the second reagent name included in the second reagent information corresponding to the first or second reagent password inputted by the reagent logon operation is set in the "second reagent" field, and "AST II" is displayed within a dialogue box 654.

When an input operation of changing the first reagent name and the second reagent name is performed, the changed reagent names are displayed within the dialogue boxes 653 and 654, and the changed reagent names are stored into the analysis information storage 41.

For example, when an input operation of setting, in the "first reagent amount" field, 150 μL as the amount of the first reagent set in the "first reagent" field to be dispensed into the reaction container 3 is performed, "150" is displayed within a dialogue box 655. When an input operation of setting, in the second reagent amount" field, 50 μL as the amount of the second reagent displayed in the "second reagent" field to be dispensed into the reaction container 3 is performed, "50" is displayed within a dialogue box 656.

The "wavelength" field is composed of fields of "wavelength 1" and "wavelength 2" for setting the wavelength of light measured by the photometric unit 13 of the analyzer 24. When an input operation of displaying a list of wavelengths in the "wavelength 1" field to select and set, from the list, a dominant wavelength at which color tone changes due to reaction between the first and second reagents displayed in the "reagent" field and each sample, "340" as a dominant wavelength (nm) is displayed within a combo box 657. Moreover, when an input operation of displaying a list of wavelengths in the "wavelength 2" field to select and set, from the list, a sub wavelength paired with the dominant wavelength set in the "wavelength 1" filed, "380" as a sub wavelength (nm) is displayed within a combo box 658.

In the "photometric point" field, an observation time to measure by the photometric unit 13 is set. When an input operation of setting a start time and an end time for measurement is performed, "20" corresponding to the start time is displayed within a dialogue box 659, and "29" corresponding to the end time is displayed within a dialogue box 660. A time point when each sample is dispensed into the reaction container 3 and the reaction container 3 rotationally moves and passes through a photometric position of the photometric unit 13 for the first time shall be a first photometric point. As a result of measurement at twentieth through twenty-ninth photometric points when the reaction container 3 containing a mixture including a tested sample passes through the photometric position for the twentieth through twenty-ninth times, analysis data is generated based on ten tested signals generated by the photometric unit 13.

The analysis parameters set on the analysis parameter setting screen 65 includes, other than the abovementioned ones, a housing position of the disk sampler 5 of the analyzer 24 that houses the sample container 17 containing a standard sample of the test item displayed in the "item" field, a density value of a test item component included in the standard sample housed in this housing position, a housing position of the disk sampler 5 that houses the sample container 17 containing a management sample for managing the test item displayed in the "item" field, a management value of a test item component included in the management sample housed in the housing position, an allowance range of the management value, etc.

Then, by an input operation via the operation part 70 of setting analysis parameters into the respective fields of the analysis parameter setting screen 65, the analysis parameter setting part 42 stores analysis parameter supplied from the system controller 80 into the analysis information storage 41 in association with the reagent information including the regent password inputted by the reagent logon screen (step S11 of FIG. 4).

Thus, it is possible to store the analysis parameters inputted in correspondence with the reagent logon operation of inputting the first and second reagent passwords owned by the operation manager into the analysis information storage 41. Consequently, it is possible to prevent a user inexperienced in how to handle analysis parameters of a test item from setting and change analysis parameters.

FIG. 8 is a view showing an example of analysis information stored in the analysis information storage 41. The analysis information storage 41 stores analysis information A1 through AN classified into N kinds of test items. Each of the analysis information A1 through AN is composed of the first reagent information of one-reagent system or the the first and second reagent information of two-reagent system and the analysis parameters stored in association with the reagent information.

The analysis information A1 stores analysis parameters such as: information a10 of "AST" that is the test item name displayed in the "item" field of the analysis parameter setting screen 65 shown in FIG. 7; information a11 of "5.0" that is set in the "sample amount" field; information a12 of "AST I" that is the reagent name set in the "first reagent" field; information a13 of "AST II" that is the reagent name set in the "second reagent" field; information a14 of "150" that is the dispensing amount set in the "first reagent amount" field; information a15 of "50" that is a dispensing amount set in the "first reagent amount"; information a15 of "50" that is a dispensing amount set in the "second reagent amount" field; information a16 of "340" that is the dominant wavelength set in the "wavelength" field; information a17 of "380" that is the sub wavelength set in the "wavelength" field; information a18 that stores information "20" corresponding to the start time set for the "observation point" field; information a19 of "29" corresponding to the end time.

Further, first reagent information is stored. The first reagent information includes: information b10 of "AST," which is the test item name written on the label 6a of the reagent container 6 shown in FIG. 3; information b11 of "AST I," which is the first reagent name; first reagent password b12 of "AST I"; information b13 of the manufacturer or distributor of "AST I"; reagent ID b14 of "AST I"; information b15 of the expiration date of "AST I"; and lot number b16 of "AST I."

Furthermore, second reagent information is stored. The second reagent information includes: information b10 of "AST," which is the test item name written on the label 7a of the reagent container 7 shown in FIG. 3; information c11 of "AST II," which is the second reagent name; second reagent password b12 of "AST II"; information b13 of the manufacturer or distributor of "AST II"; reagent ID c14 of "AST II"; information c15 of the expiration date of "AST II"; and lot number c16 of "AST II."

The analysis information A2 stores analysis parameters such as: information a20 of "TP," which is the test item name displayed in the "item" field of FIG. 5; information a21 of the dispensing amount of each sample in "TP"; information a22 of "TP I," which is the reagent name of the "first reagent"; information a24 of the dispensing amount of the first reagent in "TP I"; information a26 of the dominant wavelength; information a27 of the sub wavelength; information a28 corresponding to time to start observation; and information a29 corresponding to time to end the observation. Moreover, the analysis information A2 stores: first reagent information including: information b20 of "TP," which is the test item name written on the label 6a of the reagent container 6; information b21 of "TP I," which is the reagent name of the first reagent of one-reagent system; first reagent password b22 of "TP I"; information b23 of a manufacturer or distributor of "TP I"; reagent ID b24 of "TP I"; information b25 of the expiration date of "TP I"; and lot number b26 of "TP I."

The analysis information Ak stores analysis parameters such as: information ak20 of a test item name; information ak1 of the dispensing amount of each sample; information ak2 of the reagent name of, e.g., a first reagent of one-reagent system; information ak4 of the dispensing amount of the first reagent; information ak6 of the dominant wavelength; information ak7 of the sub wavelength; information ak8 corresponding to time to start observation; and information ak9 corresponding to time to end the observation. Moreover, the analysis information Ak stores the first reagent information including: information bk0 of a test item name written on the label 6a of the reagent container 6; information bk1 of the reagent name of the first reagent; first reagent password bk2 of the first reagent; information bk3 of a manufacturer or distributor of the first reagent; reagent ID bk4 of the first reagent; information bk5 of the expiration date of "the first reagent; and lot number b26 of the first reagent.

Next, a user account to be identification of an operator as a user authorized to access the automatic analyzing apparatus 100 is registered by the operation manager so that daily tests can be executed by the automatic analyzing apparatus 100. The user accounts to be registered are: a first user account composed of a user name, a password paired with the user name, and a first or second reagent password; and a second user account composed of a user name and a password paired with the user.

When an operation of displaying the user account registration screen is performed via the operation part 70, the registering part 43 causes the display 62 to display the user account registration screen (step S12 of FIG. 4).

FIG. 9 is a view showing an example of the user account registration screen displayed on the display 62. A user account registration screen 66 is composed of fields of "user name," "password," and "reagent password" for registering the user account of the operator. By the registering operation via the operation part 70, the inputted user account is registered and stored into the registering part 43.

A range operable by the automatic analyzing apparatus 100 is divided into a first range narrower than that of the operation manager capable of daily tests, and a second range narrower than the first range.

The operation manager gives a second operator a second range access right. The second operator is unfamiliar with handling of analysis parameters of all the analyzable test items. Consequently, it is possible to register the second user account for the second user.

Further, the operation manager permits a first operator to possess first or second reagent passwords of the same number as that of the kinds of familiar test items, and gives the first operator a first range access right that includes the second range access right and additionally an access right by the reagent passwords permitted to possess. The first operator is familiar with handling of analysis parameters of at least one kind of test item. Consequently, it is possible to register the first or second user account for the first operator.

When an input operation of registering a user name into the "user name" field via the operation part 70 is performed, the user name is displayed within a dialogue box 661. When an input operation of registering the user name of the first operator is performed, the user name of the first operator such as "taro" is displayed within the dialogue box 661. When an input operation of registering the user name of the second operator is performed, the user name of the second operator such as "jiro" is displayed within the dialogue box 661.

When an input operation of registering, into the "password" field, a password paired with the user name registered in the "user name" field is performed, the password masked with "******" is displayed within a dialogue box 662.

When an input operation of registering, into the "reagent password" field, a first or second password given by the operation manager to the first operator registered in the "user name" and "password" fields is performed, one or more reagent passwords masked with "*****" are displayed within a combo box 663.

Thus, it is possible to give the second operator the second range access right, whereby the second operator can execute daily tests of an operable range in the automatic analyzing apparatus 100. Then, it is possible to register a second user account with the access right.

Consequently, it is possible to prevent the second operator from setting and changing the analysis parameters of all the test items.

Further, it is possible to give the first operator the first range access right that includes the second range access right and additionally an access right by first or second reagent passwords of the same number as that of the types of familiar test items. Then, it is possible to register a first user account with the access right, or the second user account.

Consequently, it is possible to prevent the first operator from changing the analysis parameters of a test item associated with a first or second reagent password that the first operator does not possess.

The registering part 43 registers and stores the user account supplied from the system controller 80 in response to the input operation of registering the user account via the operation part 70, and first range or second range information corresponding to the user account (step S13 of FIG. 4).

Then, when an operation of turning off the power via the operation part 70 is performed after the registration of the user account ends, the system controller 80 instructs the analysis controller 30 and the analysis information part 40 to stop, and the automatic analyzing apparatus 100 thereby ends the operation.

Next, a user logon operation of bringing the automatic analyzing apparatus 100 into an operable state and an operation of the automatic analyzing apparatus 100 in response to the user logon operation will be described.

(Example of User Logon Process)

FIG. 10 is a flowchart showing the user logon operation and the operation of the automatic analyzing apparatus 100 in response to the user logon operation. Instead of steps S5 through S6, the process of the flowchart is executed after steps S1 through S4 shown in FIG. 4.

Although input information is inputted for every reagent in the above embodiment, the user logon operation substitutes for the input of the input information in this example. When an operation of turning on the power via the operation part 70 is performed to actuate the automatic analyzing apparatus 100, the automatic analyzing apparatus 100 starts operation. After the operation starts, reagent information is read (S1), the reagent information is stored (S2), the reagent information is displayed (S3), and a reagent is selected (S4). This process is the same as in steps S1 through S4 of FIG. 4.

The system controller 80 causes the display 62 to display a user logon screen (step S21).

FIG. 11 is a view showing an example of the user logon screen displayed on the display 62. A user logon screen 67 is composed of fields of "user name," "password" and "reagent password" for setting the user account of the operator.

Next, the account is inputted. The account is identified by a user name and a password for confirming each user (step S22). When an input operation of setting, into the "user name" field, the user name of the first user registered in the registering part 43 is performed, "taro" is displayed within a dialogue box 671. When an input operation of setting the user name of the second user registered in the registering part 43 is performed, "jiro" is displayed within the dialogue box 671.

When an input operation of setting, into the "password" field, a password registered in pair with the user name set in the "user name" field is performed, "******" masking the password is displayed within a dialogue box 672.

When the account is thus inputted, the system controller 80 refers to the password stored in association with the account. For example, in a case that logon was made with a certain account and a reagent password was inputted, the inputted reagent password has been stored in the system controller 80 in association with the account and the reagent.

Then, in a case that the account is inputted as described above, the reagent password associated with the inputted account and the reagent selected in step S4 is searched. Then, the system controller 80 inputs the searched reagent password.

When an operation of inputting, into the "reagent password" field, one or more first or second reagent passwords included in the first range is performed by the operator, "***" masking the reagent password is displayed within a combo box 673. In a case that a reagent password is not searched by the system controller 80, the reagent password is not automatically inputted because the reagent password is not stored in association with the inputted account or selected reagent. In this case, it is necessary to input the reagent password as in step S6 of FIG. 4**.

In this embodiment, it is possible to omit input of a reagent password by input of an account as described above. However, after a reagent password is inputted by the system controller 80, the same process as in FIG. 4 is executed. Therefore, the process then proceeds to step S7, and the process after reference of the reagent password is executed.

(Example of Restriction of Permission by Account)

In the above example, automatic input of a reagent password is described. However, a low-level user may be refused to set/change analysis parameters before a reagent password is cross-checked at the time that an account is inputted, and a high-level user may be permitted to set/change analysis parameters without the need for cross-check of a reagent password. The above example is described from the viewpoint that middle-level users should be separately authorized depending on reagents. However, low-level users do not need to input passwords, whereas high-level users do not need to be confirmed for every reagent.

Therefore, for low-level and high-level users, it is possible by omitting an operation of cross-checking a password to make the process less complicated in a case that the operator forgets or mistakenly inputs a password.

FIG. 12 is a flowchart showing the operation of the automatic analyzing apparatus in response to the user logon operation according to the embodiment of the present invention. First, display of the user logon screen (step S21) and input of an account (step S22) are executed.

However, since this process is the same as in steps S21 and S22 of FIG. 10, the description will be omitted.

Next, it is determined whether the account is a permitted account or not (step S31). In the case of a high-level user (step S31: high-level), the user can proceed to an analysis/measurement process in step S35 without the need for cross-check of a password by acquisition of cross-check information and input of input information, because a process for manager, which enables operation without precise input, is also required. In the case of a middle-level user (first user), the user is permitted to set/change analysis parameters after confirmation of a reagent password. In the case of a low-level user (second user), the user is not permitted to set/change analysis parameters, and the operation is ended. The low-level user and the middle-level user will be referred to as the first user and the second user in the following description.

When an operation of inputting a second user account of the second operator registered in the registering part 43 is performed via the operation part 70 (step S31: low-level), the system controller 80 supplies the second user account inputted via the operation part 70 to the registering part 43. The registering part 43 outputs second range information corresponding to the second user account supplied by the system controller 80, to the system controller 80 and the analysis parameter setting part 42.

The system controller 80 causes the display 62 to display a screen that makes the automatic analyzing apparatus 100 operable, based on the second range information outputted by the registering part 43. Based on the second range information outputted by the registering part 43, the analysis parameter setting part 42 refuses storing of analysis parameters supplied by the system controller 80 into the analysis information storage 41 and precludes the setting and change of analysis parameters, after an operation of displaying the analysis parameter setting screen is performed via the operation part 70 (step S32). Consequently, the user is not permitted to set/change analysis parameters, and a series of processes are finished.

When an unregistered user account is supplied by the system controller 80 to the registering part 43, for example, a warning message like "Inputted user account is not registered," is displayed on the displayed 62.

Thus, it is possible to preclude the setting and change of analysis parameters in a state that the automatic analyzing apparatus 100 is operable after the second user account of the second operator is inputted.

Consequently, it is possible to prevent the second operator from the setting and change of analysis parameters.

When a user logon operation of inputting a user name and password included in the first user account registered in the registering part 43 is performed via the operation part 70 (step S31: middle-level), the system controller 80 supplies the user name and password inputted via the operation part 70 to the registering part 43. The registering part 43 outputs first range information corresponding to the user name and password supplied from the system controller 80 to the system controller 80 and the analysis parameter setting part 42. Based on the first range information outputted by the registering part 43, the system controller 80 causes the display 62 to display a screen that makes the automatic analyzing apparatus 100 operable. Based on first or second reagent password included in the first range information outputted by the registering part 43, the analysis parameter setting part 42 enables the setting or change of analysis parameters after an operation of displaying the analysis parameter setting screen associated with the reagent password is performed (step S33). A state that analysis parameters can be set or changed is released by a reagent logoff operation of precluding the setting and change of analysis parameters, a user logoff operation of making the automatic analyzing apparatus 100 inoperable, or an operation of turning off the power, via the operation part 70.

After that, reagent logon and analysis/measurement in steps S34 through S35 are executed, and then an account registration process is executed. In the account registration, the system controller 80 supplies the user name and password of the second operator inputted via the operation part 70 to the registering part 43, and also supplies the first or second reagent password of the first operator to the analysis parameter setting part 42. The registering part 43 outputs operable second range information corresponding to the user name and password supplied from the system controller 80, to the system controller 80. The system controller 80 causes the display 62 to display a screen that makes the automatic analyzing apparatus 100 operable, based on the second range information outputted by the registering part 43. Based on the reagent password supplied by the system controller 80, the analysis parameter setting part 42 enables the setting and change of analysis parameters after the operation of displaying the analysis parameter setting screen associated with the reagent password is performed via the operation part 70.

By thus registering a first user account, it is possible to set or change analysis parameters of a test item associated with the first or second reagent password included in the registered first user account, in a state that the automatic analyzing apparatus 100 is operable after the user name and password in which the first or second reagent password is excluded from the first user account. Consequently, it is possible to save time for the operation of inputting the first or second reagent password for every user logon operation.

The description of the process of setting/changing analysis parameters will continue. The operation proceeds to step S34, where a reagent logon process is executed (step S34). Although this reagent logon process is similar to those in steps S1 through S8 of FIG. 4, it will be described again. After the user logon operation, the reagent container 6 containing the first reagent and the reagent container 7 containing the second reagent used in the automatic analyzing apparatus 100 are housed in the first and second reagent storages 1 and 2. When an operation of reading the respective reagent information of the housed reagent containers 6 and 7 is performed via the operation part 70, the system controller 80 instructs the analysis mechanism 30 and the analysis information part 40 to collect the reagent information. The controller 32 controls the mechanism part 31 to activate the racks 1a and 2a and the readers 1b and 2b of the first and second reagent storages 1, 2.

The readers 1b and 2b read the first and second reagent information from the labels 6a and 7a of the reagent containers 6 and 7 held by the rotating racks 1a and 2a, and output to the controller 32. The controller 32 adds, to the first and second reagent information outputted from the readers 1b and 2b, information of the housing positions of the first and second reagent storages 1, 2 holding the reagent containers 6 and 7 having the first and second reagent information are housed, and outputs to the reagent managing part 44.

When an operation of displaying a reagent management screen is performed via the operation part 70 to confirm the first and second reagents housed in the first and second reagent storages 1 and 2 after the reading of the reagent information is finished, the reagent managing part 44 cross-checks the reagent IDs included in the first and second reagent information outputted by the controller 32 with the reagent IDs stored in the analysis information storage 41. Then, the reagent managing part 44 identifies, among the first and second reagent information outputted from the controller 32, the first and second reagent information having reagent IDs coincident with the reagent IDs stored in the analysis information storage 41, and causes the display 62 to display a reagent management screen for displaying the reagent information in which the first and second reagent passwords are excluded from the first and second reagent information outputted from the controller 32.

FIG. 13 is a view showing an example of the reagent management screen displayed on the display 62. A reagent management screen 68 is, similarly to the reagent information display screen 63 shown in FIG. 5, composed of fields of sequential numbers "1" through "m" and fields of "item," "reagent," "position," "expiration date," "ID," "manufacturer," etc., corresponding to the respective fields "1" through "m." Then, the first and second reagent information obtained by identifying reagent information including the first and second reagent information displayed in the fields "1" through "3" of the reagent information display screen 63 stored in the analysis information storage 41 are displayed.

Thus, it is possible to confirm the first and second reagent information of the first and second reagents housed in the first and second reagent storages 1 and 2, from the first and second reagent information displayed on the reagent management screen 68 of the display 62.

Further, it is possible to display reagent information of a reagent of an analyzable test item stored in the analysis information storage 41 by identifying from the first and second reagents housed in the first and second reagent storages 1 and 2. Consequently, when an unnecessary reagent unsuitable for the automatic analyzing apparatus 100 is included, it is possible to easily find it.

Furthermore, by hiding the first and second reagent passwords, it is possible to prevent the first operator from changing analysis parameters of a test item associated with a first or second reagent password that the first operator does not possess. Moreover, it is possible to prevent the second operator from changing analysis parameters of a test item.

Next, an operation in a case that there is a need for changing analysis parameters will be described. In the automatic analyzing apparatus 100 to which the second operator has made logon by the second operator's account, the first operator changes analysis parameters. When a first operator having a first or second reagent password associated with analysis parameters required to change executes an operation of displaying a reagent logon screen via the operation part 70, the system controller 80 causes the display 62 to display the reagent logon screen.

The reagent logon screen displayed on the display 62 for changing analysis parameters is the same as that shown in FIG. 6. The reagent logon screen 64 is composed of a field of "reagent password" in which it is possible to input a plurality of first or second reagent passwords.

For example, when a first operator capable of changing analysis parameters of a test item displayed on the analysis parameter setting screen 65 executes a reagent logon operation of inputting a first or second reagent password of the test item, "*****" masking the reagent password is displayed within a combo box 641.

Next, the analysis/measurement process is executed (step S35).

Although the analysis/measurement process is similar to the process in steps S9 through S11 of FIG. 4, the description will be made again. The system controller 80 supplies the inputted reagent password to the analysis parameter setting part 42. The analysis parameter setting part 42 reads out analysis parameters associated with the reagent password supplied from the system controller 80, from the analysis information storage 41. Next, the system controller 80 causes the display 62 to display an analysis parameter setting screen on which it is possible to change parameters including the read-out analysis parameters.

When an operation of changing analysis parameter is performed via the operation part 70, the system controller 80 supplies the changed analysis parameters to the analysis parameter setting part 42. The analysis parameter setting part 42 stores analysis parameters in which changed parts of the analysis parameters having been read are replaced with the changed analysis parameters supplied from the system controller 80, into the analysis information storage 41.

Thus, by the reagent logon operation of inputting the first or second reagent password, it is possible to cause the display 62 to display the analysis parameter setting screen that enables change of analysis parameters of a test item associated with the reagent password.

Consequently, it is possible to prevent a first operator from changing analysis parameters of a test item associated with a first or second reagent password that the first operator does not possess.

Moreover, it is possible to prevent a second operator from changing analysis parameters of a test item.

Calibration data generated by measurement of a mixture including a standard sample of each test item having become analyzable by the setting and change of analysis parameters is stored in the data storage 51 of the data processor 50. Then, when an operation of analyzing each test item is performed via the operation part 70 after a test item to be tested is set for every tested sample, based on the analysis parameters stored in the analysis information storage 41, the controller 32 controls the mechanism part 31 to activate each analysis unit of the analyzer 24. The analyzer 24 dispenses the tested sample and a reagent for the test item of the tested sample into the reaction container 3, and measures the mixture. Then, a tested signal generated by this measurement is outputted to the computing part 51 of the data processor 50. The computing part 51 generates analysis data from the tested signal outputted by the analyzer 24 and outputs to the output part 60.

Then, the aforementioned account registration process is executed, and the series of processes are ended. That is to say, when the analysis data is outputted to the output part 60, the system controller 80 instructs the analysis controller 30, the analysis information part 40, the data processor 50 and the output part 60 to stop the measurement. Next, when an operation of turning off the power is performed via the operation part 70, the automatic analyzing apparatus 100 ends the operation.

According to the embodiment of the present invention described above, it is possible to house the reagent containers 6 and 7 containing the first and second reagents for each analyzable test item, into the first and second reagent storages 1 and 2, cause the readers 1*b* and 2*b* to read the first and second reagent information written on the housed reagent containers 6 and 7, and stores into the analysis information storage 41.

Then, by authorizing a second operator to access a second range access and registering a second user account, it is possible to preclude the setting and change of analysis parameters of all analyzable test items in a state that the automatic analyzing apparatus 100 is operable after the registered second user account is inputted.

Further, by authorizing a first operator to access a first range including first or second reagent passwords of the same number as that of the types of familiar test items in addition to the second range, and registering a first user account, it is possible to set or change analysis parameters of a test item associated with the registered reagent password without the need for inputting the first and second reagent passwords, in a state that the automatic analyzing apparatus 100 is operable after the user name and password included in the registered first user account are inputted. Consequently, it is possible to save time for the operation of inputting the first or second reagent password after user logon. Moreover, it is possible to prevent the first operator from setting and changing analysis parameters of a test item associated with a first or second reagent password that the first operator does not possess.

Furthermore, in a case that a first or second reagent password is inputted through a reagent logon operation by a first operator and, on the other hand, the first or second reagent password has been stored in the analysis information storage 41, it is possible to enable the setting or change of analysis parameters of a test item associated with the reagent password, and store, into the analysis information storage 41, the analysis parameters inputted by the setting or change in association with reagent information including the inputted reagent password.

Consequently, it is possible to prevent the first operator from changing analysis parameters of a test item associated with a first or second reagent password that the first operator does not possess.

Moreover, it is possible to prevent a second operator from setting and changing analysis parameters of a test item.

Still further, it is possible to confirm first and second reagent information of first and second reagents housed in the first reagent storage 1 and the second reagent storage 2, from the first and second reagent information displayed on the reagent information display screen 63 and the reagent management screen 68 of the display 62. Moreover, by hiding first and second reagent passwords included in first and second reagent information read from first and second reagents housed in the first reagent storage 1 and the second reagent storage 2, it is possible to prevent a first operator from changing analysis parameters of a test item associated with a first or second reagent password that the first operator does not possess. Moreover, it is possible to prevent a second operator from changing analysis parameters of a test item.

As described above, prevention of improper setting or changing the analysis parameter is enabled and precise analysis of each examination term becomes possible.

Figure 14:
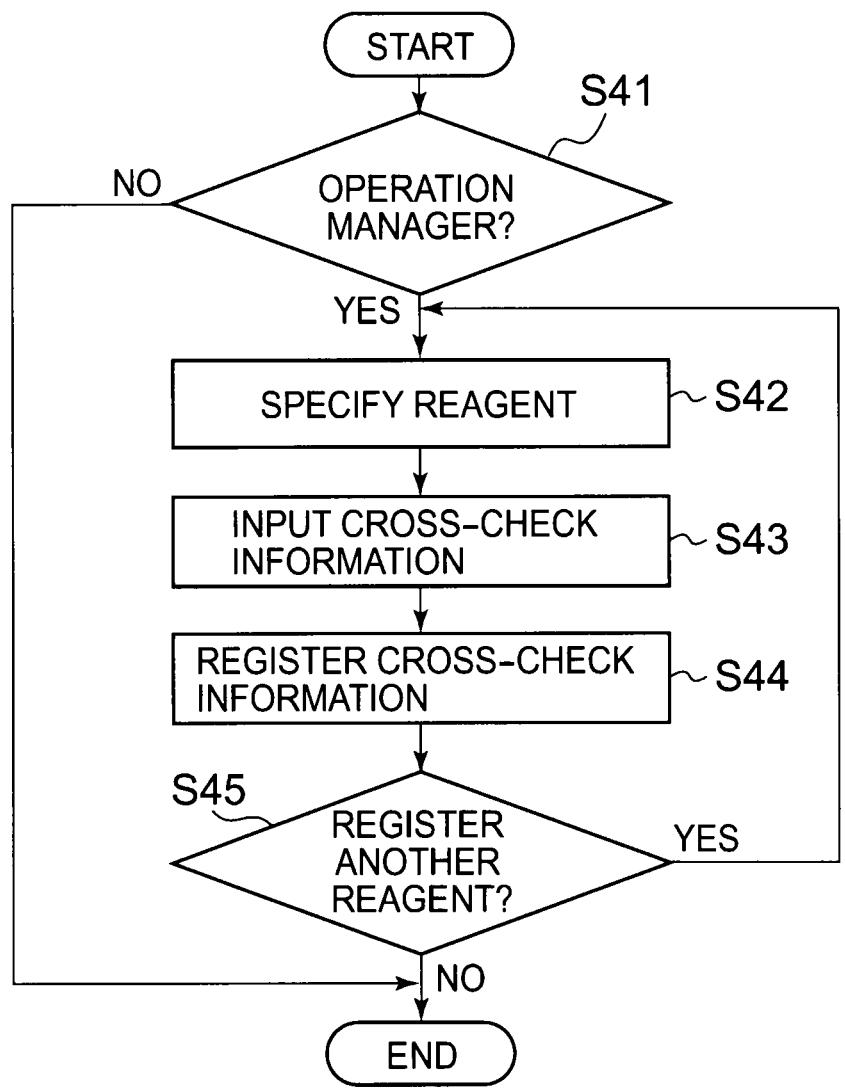
FIG. 14 is a flowchart describing the setting of a password by an operation manager.

FIG. 14 is a flowchart describing password setting by the operation manager. Although the password setting by the operation manager is referred to in step S3 of FIG. 4, the detailed description will be made here. First, it is determined whether an operator is an operation manager or not (step S41). The operator may be identified by inputting an account and password and, in this case, similar processes to those in steps S21 and S22 of FIG. 10 may be employed.

Next, a reagent is specified (step S42). The reagent can be specified by input of information specifying the reagent such as the reagent name by the operation manager, but may be specified by reading a barcode put on the reagent. Next, cross-check information is inputted (step S43). This cross-check information is, for example, the aforementioned password. Consequently, cross-check information unique to the specified reagent is inputted.

Then, the cross-check information is registered (step S44). Since the reagent and the cross-check information are associated as described above, the cross-check information is registered with this association.

Besides, it is determined whether more registration of cross-check information is required or not (step S45). After the registration is finished, a screen for confirming whether more registration is required is displayed, and input by the operation manager is accepted. When the need for more registration is inputted (step S45: Yes), the operation returns to step S42, and a similar process is repeated for another reagent. When end of the registration is inputted (step S45: No), the series of the processes are finished.

The analysis information part 40 may be provided with a decoder that converts the first and second reagent passwords of the first and second reagent information attached to the labels 6*a* and 6*b* of the reagent containers 6 and 7 into first and second code passwords coded by using a coding key, and that decodes the first and second code passwords into the first and second reagent passwords by using a decoding key. Then, the first and second reagent information that the first and second passwords included in the first and second reagent information outputted from the controller 32 of the analysis controller 30 are decoded by the decoder is outputted to the reagent managing part 44. Consequently, it is possible to prevent that the first and second reagent passwords written on the reagent container 6 and 7 are decoded by an apparatus other than the automatic analyzing apparatus 100, and it is possible to increase security of the first and second reagent passwords.

What is claimed is:

1. An apparatus, comprising:
    a display;
    a sample dispensing probe configured to dispense a sample;
    a reagent dispensing probe configured to dispense a reagent to be mixed with the sample in a mixture; and
    circuitry programmed to
        receive selected information identifying the reagent to be analyzed in the mixture of the sample and the reagent, and receive an input password via an input screen,
        determine, after receiving the input password, whether an account of a user corresponds to one of at least a middle-level account and a high-level account, acquire a cross-check password, which is associated with information written on a reagent container containing the reagent, unique to the kind of the reagent selected in response to determining that the account of the user corresponds to the middle-level account, determine whether to permit input of data in the analyzing process by comparing the cross-check password and the input password to determine whether the input password equates to the cross-check password, and determine to permit the input of the data in response to determining that the account of the user corresponds to the high-level account, and
        in response to the circuitry determining to permit the input of the data, the circuitry being further programmed to
            display, on the display, an analysis parameter setting screen for the input of the data together with analysis parameters corresponding to reagent information of the reagent, which include amount of the reagent, determined based on test items,
            accept the input of the data in the analyzing process,
            store the input analysis parameters corresponding to reagent information of the reagent, reflect the data input through the analysis parameter setting screen on the analysis parameters, and
            based on the analysis parameter reflecting the inputted data, receive a measure of the mixture of the sample and the reagent, to thereby generate analysis data.

2. The apparatus according to claim 1, wherein the circuitry is programmed to acquire the cross-check password from an inspection of the information written on the reagent container containing the reagent.

3. The apparatus according to claim 1, wherein the circuitry is programmed to, when the circuitry determines not to permit the input of the data, refuse to accept the input of the data setting the analysis parameter of the reagent.

4. The apparatus according to claim 1,
    wherein
    the circuitry obtains reagent information representing a property of the reagent by inspecting the reagent container containing the reagent, and
    the display displays the reagent information.

5. The apparatus according to claim 1,
    wherein the circuitry is programmed to input an account of a user, wherein in a case that the account inputted by the circuitry is an account not to be permitted, the circuitry is programmed to determine not to permit the input of the data of the reagent.

6. The apparatus according to claim 1, further comprising:
    a storage configured to store the input password in association with an account of a user, wherein
    the circuitry is programmed to
        input the account of the user, and
        read out the input password stored in association with the inputted account from the storage and input the input password.

7. The apparatus according to claim 1, wherein
    the circuitry is programmed to determine whether the account of the user corresponds to one of a low-level account, the middle-level account, and the high-level account.

8. The apparatus according to claim 1, wherein the reagent information includes an expiration date of the reagent, an identification number of the reagent, and a manufacturer of the reagent.

9. An apparatus, comprising:
    a display;
    a sample dispensing probe configured to dispense a sample;
    a reagent dispensing probe configured to dispense a reagent to be mixed with the sample in a mixture;
    an operation part programmed to receive selected information identifying the reagent to be analyzed in the mixture of the sample and the reagent, and to receive an input password via an input screen;
    a system controller programmed to determine, after receiving the input password, whether an account of a user corresponds to one of at least a middle-level account and a high-level account, programmed to acquire a cross-check password, which is associated with information written on a reagent container containing the reagent, unique to the kind of the reagent selected in response to determining that the account of the user corresponds to the middle-level account, programmed to determine whether to permit input of data in the analyzing process by comparing the cross-check password and the input password to determine whether the input password equates to the cross-check password, and programmed to determine to permit the input of the data in response to determining that the account of the user corresponds to the high-level account; and
    an analysis information part programmed to, in response to the system controller determining to permit the input of the data,
        display, on the display, an analysis parameter setting screen corresponding to reagent information of the reagent for the input of the data together with analysis parameters corresponding to reagent information of the reagent, which include amount of the reagent, determined based on test items,
        accept the input of the data in the analyzing process, to store the input analysis parameters corresponding to reagent information of the reagent, to reflect the data input through the analysis parameter setting screen on the analysis parameters, and
        based on the analysis parameter reflecting the inputted data, receive a measure of the mixture of the sample and the reagent, to thereby generate analysis data.

10. The apparatus according to claim 1, wherein an analysis parameter setting screen associated with a first reagent is different from an analysis parameter setting screen associated with a second reagent.

11. A method for an apparatus that includes a display, a sample dispensing probe configured to dispense a sample, a reagent dispensing probe configured to dispense a reagent to be mixed with the sample in a mixture, and circuitry, the method comprising:

receiving, by the circuitry, selected information identifying the reagent to be analyzed in the mixture of the sample and the reagent, and receiving an input password via an input screen;

determining, by the circuitry, after receiving the input password, whether an account of a user corresponds to one of at least a middle-level account and a high-level account, acquiring a cross-check password, which is associated with information written on a reagent container containing the reagent, unique to the kind of the reagent selected in response to determining that the account of the user corresponds to the middle-level account, determining whether to permit input of data in the analyzing process by comparing the cross-check password and the input password to determine whether the input password equates to the cross-check password, and determining to permit the input of the data in response to determining that the account of the user corresponds to the high-level account; and in response to determining to permit the input of the data,
displaying, on the display, an analysis parameter setting screen for the input of the data together with analysis parameters corresponding to reagent information of the reagent, which include amount of the reagent, determined based on test items, accepting, by the circuitry, the input of the data in the analyzing process, storing the input analysis parameters corresponding to reagent information of the reagent, reflecting the data input through the analysis parameter setting screen on the analysis parameters, and based on the analysis parameter reflecting the inputted data, receiving, by the circuitry, a measure of the mixture of the sample and the reagent, to thereby generate analysis data.

\* \* \* \* \*